US011547855B2

(12) United States Patent
Dinsmoor et al.

(10) Patent No.: US 11,547,855 B2
(45) Date of Patent: Jan. 10, 2023

(54) ECAP SENSING FOR HIGH FREQUENCY NEUROSTIMULATION

(71) Applicant: Medtronic, Inc., Minneapolis, MN (US)

(72) Inventors: David A. Dinsmoor, North Oaks, MN (US); Christopher L. Pulliam, Plymouth, MN (US); Hank Bink, Golden Valley, MN (US); Kristin N. Hageman, Dayton, MN (US)

(73) Assignee: Medtronic, Inc., Minneapolis, MN (US)

( * ) Notice: Subject to any disclaimer, the term of this patent is extended or adjusted under 35 U.S.C. 154(b) by 112 days.

(21) Appl. No.: 17/065,282

(22) Filed: Oct. 7, 2020

(65) Prior Publication Data
US 2021/0121700 A1    Apr. 29, 2021

Related U.S. Application Data

(60) Provisional application No. 62/926,164, filed on Oct. 25, 2019.

(51) Int. Cl.
*A61N 1/36*    (2006.01)
(52) U.S. Cl.
CPC ..... *A61N 1/36157* (2013.01); *A61N 1/36062* (2017.08); *A61N 1/36067* (2013.01);
(Continued)
(58) Field of Classification Search
CPC ............ A61N 1/36157; A61N 1/36062; A61N 1/36067; A61N 1/36071; A61N 1/36139;
(Continued)

(56) References Cited

U.S. PATENT DOCUMENTS 5,603,726 A    2/1997    Schulman et al.
5,800,465 A    9/1998    Thompson et al.
(Continued)

FOREIGN PATENT DOCUMENTS

EP    2396072 B1    3/2013
EP    3013413 A1    5/2016
(Continued)

OTHER PUBLICATIONS

Agnesi et al., "Local Glutamate Release in the Rat Ventral Lateral Thalamus Evoked by High-Frequency Stimulation," Journal of Neural Engineering, vol. 7, No. 2, Apr. 2010, 20 pp.
(Continued)

*Primary Examiner* — Eugene T Wu
(74) *Attorney, Agent, or Firm* — Shumaker & Sieffert, P.A.

(57) ABSTRACT

Techniques are disclosed for implementing the use of electrically evoked compound action potentials (ECAPs) to adaptively adjust parameters of high frequency electrical stimulation. In one example, a medical device delivers electrical stimulation therapy comprising a train of electrical stimulation pulses to a patient, wherein the train of electrical stimulation pulses comprises a pulse frequency greater than or equal to 500 Hertz. After delivering the train of electrical stimulation pulses, the medical device ceases delivery of the high frequency electrical stimulation therapy for a predetermined period of time. During the predetermined period of time, the medical device senses an ECAP from the patient and determines, based on the sensed ECAP, a value of a parameter at least partially defining the train of electrical stimulation pulses. Responsive to the predetermined period of time elapsing, the medical device resumes delivery of the high frequency electrical stimulation according to the determined parameter.

20 Claims, 8 Drawing Sheets

(52) U.S. Cl.
CPC ..... *A61N 1/36071* (2013.01); *A61N 1/36139* (2013.01); *A61N 1/36164* (2013.01); *A61N 1/36175* (2013.01); *A61N 1/36178* (2013.01); *A61N 1/36171* (2013.01)

(58) Field of Classification Search
CPC ............ A61N 1/36164; A61N 1/36175; A61N 1/36178; A61N 1/36171
See application file for complete search history.

(56) References Cited

U.S. PATENT DOCUMENTS

| | | | |
|---|---|---|---|
| 6,157,861 | A | 12/2000 | Faltys et al. |
| 6,205,360 | B1 | 3/2001 | Carter |
| 6,289,247 | B1 | 9/2001 | Faltys et al. |
| 6,314,325 | B1 | 11/2001 | Fitz |
| 6,421,566 | B1 | 7/2002 | Holsheimer |
| 6,505,078 | B1 | 1/2003 | King et al. |
| 6,675,046 | B2 | 1/2004 | Holsheimer |
| 6,850,802 | B2 | 2/2005 | Holsheimer |
| 6,988,006 | B2 | 1/2006 | King et al. |
| 7,076,292 | B2 | 7/2006 | Forsberg |
| 7,206,640 | B1 | 4/2007 | Overstreet |
| 7,333,858 | B2 | 2/2008 | Killian et al. |
| 7,577,480 | B2 | 8/2009 | Zeijlemaker |
| 7,616,999 | B2 | 11/2009 | Overstreet et al. |
| 7,657,318 | B2 | 2/2010 | King et al. |
| 7,689,289 | B2 | 3/2010 | King |
| 7,742,810 | B2 | 6/2010 | Moffitt et al. |
| 7,792,583 | B2 | 9/2010 | Miesel et al. |
| 8,036,747 | B2 | 10/2011 | Thacker et al. |
| 8,090,446 | B2 | 1/2012 | Fowler et al. |
| 8,504,150 | B2 | 8/2013 | Skelton |
| 8,620,441 | B2 | 12/2013 | Greenberg et al. |
| 8,676,329 | B2 | 3/2014 | Wacnik et al. |
| 8,694,108 | B2 | 4/2014 | Alataris et al. |
| 8,708,934 | B2 | 4/2014 | Skelton et al. |
| 8,712,533 | B2 | 4/2014 | Alataris et al. |
| 8,712,534 | B2 | 4/2014 | Wei |
| 8,751,009 | B2 | 6/2014 | Wacnik |
| 8,897,888 | B2 | 11/2014 | Parker et al. |
| 8,923,984 | B2 | 12/2014 | Parker et al. |
| 9,002,460 | B2 | 4/2015 | Parker |
| 9,072,910 | B2 | 7/2015 | Parker et al. |
| 9,089,714 | B2 | 7/2015 | Robinson |
| 9,089,715 | B2 | 7/2015 | Parker et al. |
| 9,138,582 | B2 | 9/2015 | Doan et al. |
| 9,155,892 | B2 | 10/2015 | Parker et al. |
| 9,283,373 | B2 | 3/2016 | Parker et al. |
| 9,302,112 | B2 | 4/2016 | Bornzin et al. |
| 9,339,655 | B2 | 5/2016 | Carbunaru |
| 9,364,667 | B1 | 6/2016 | Dinsmoor et al. |
| 9,381,356 | B2 | 7/2016 | Parker et al. |
| 9,386,934 | B2 | 7/2016 | Parker et al. |
| 9,387,325 | B1 | 7/2016 | Min et al. |
| 9,566,439 | B2 | 2/2017 | Single et al. |
| 9,597,507 | B2 | 3/2017 | Johanek et al. |
| 9,700,713 | B2 | 7/2017 | Robinson et al. |
| 9,872,990 | B2 | 1/2018 | Parker et al. |
| 9,993,646 | B2 | 6/2018 | Parramon et al. |
| 10,569,088 | B2 | 2/2020 | Dinsmoor et al. |
| 10,933,242 | B2 | 3/2021 | Torgerson |
| 2004/0267333 | A1 | 12/2004 | Kronberg |
| 2008/0221640 | A1 | 9/2008 | Overstreet et al. |
| 2008/0300655 | A1* | 12/2008 | Cholette ............ A61N 1/36135 607/60 |
| 2011/0054570 | A1 | 3/2011 | Lane |
| 2011/0071589 | A1 | 3/2011 | Starkebaum et al. |
| 2011/0077712 | A1 | 3/2011 | Killian |
| 2011/0125223 | A1 | 5/2011 | Carbunaru et al. |
| 2011/0184488 | A1* | 7/2011 | De Ridder ......... A61N 1/36071 607/46 |
| 2012/0155188 | A1 | 6/2012 | Buettner et al. |
| 2013/0208390 | A1 | 8/2013 | Singh et al. |
| 2013/0268021 | A1 | 10/2013 | Moffitt |
| 2013/0289664 | A1 | 10/2013 | Johanek |
| 2013/0289683 | A1 | 10/2013 | Parker et al. |
| 2014/0005753 | A1 | 1/2014 | Carbunaru |
| 2014/0025146 | A1 | 1/2014 | Alataris et al. |
| 2014/0031896 | A1 | 1/2014 | Alataris et al. |
| 2014/0031905 | A1 | 1/2014 | Irazoqui et al. |
| 2014/0074189 | A1 | 3/2014 | Moffitt |
| 2014/0142656 | A1 | 5/2014 | Alataris et al. |
| 2014/0142673 | A1 | 5/2014 | Alataris et al. |
| 2014/0194772 | A1 | 7/2014 | Single et al. |
| 2014/0236042 | A1 | 8/2014 | Parker et al. |
| 2014/0236257 | A1 | 8/2014 | Parker et al. |
| 2014/0243924 | A1 | 8/2014 | Zhu et al. |
| 2014/0243926 | A1 | 8/2014 | Carcieri et al. |
| 2014/0243931 | A1 | 8/2014 | Parker et al. |
| 2014/0277282 | A1 | 9/2014 | Jaax |
| 2014/0288577 | A1 | 9/2014 | Robinson et al. |
| 2014/0293737 | A1 | 10/2014 | Parker et al. |
| 2014/0296936 | A1 | 10/2014 | Alataris et al. |
| 2014/0324143 | A1 | 10/2014 | Robinson et al. |
| 2014/0371813 | A1 | 12/2014 | King et al. |
| 2014/0378941 | A1 | 12/2014 | Su et al. |
| 2014/0379043 | A1 | 12/2014 | Howard |
| 2015/0005842 | A1 | 1/2015 | Lee et al. |
| 2015/0012068 | A1 | 1/2015 | Bradley et al. |
| 2015/0032181 | A1* | 1/2015 | Baynham ............ A61N 1/36139 607/46 |
| 2015/0057729 | A1 | 2/2015 | Parker et al. |
| 2015/0127062 | A1 | 5/2015 | Holley et al. |
| 2015/0179177 | A1 | 6/2015 | Nagao |
| 2015/0282725 | A1 | 10/2015 | Single |
| 2015/0313487 | A1 | 11/2015 | Single et al. |
| 2015/0360031 | A1 | 12/2015 | Bornzin et al. |
| 2015/0374999 | A1 | 12/2015 | Parker et al. |
| 2016/0082252 | A1 | 3/2016 | Hershey et al. |
| 2016/0121124 | A1 | 5/2016 | Johanek et al. |
| 2016/0129272 | A1 | 5/2016 | Hou et al. |
| 2016/0136420 | A1 | 5/2016 | Brink et al. |
| 2016/0157769 | A1 | 6/2016 | Min et al. |
| 2016/0158550 | A1 | 6/2016 | Hou et al. |
| 2016/0166164 | A1 | 6/2016 | Obradovic et al. |
| 2016/0175594 | A1 | 6/2016 | Min et al. |
| 2016/0206883 | A1 | 7/2016 | Bornzin et al. |
| 2016/0287126 | A1 | 10/2016 | Parker et al. |
| 2016/0287182 | A1 | 10/2016 | Single |
| 2016/0346534 | A1 | 12/2016 | Isaacson et al. |
| 2016/0361542 | A1 | 12/2016 | Kaula et al. |
| 2017/0001017 | A9 | 1/2017 | Parker et al. |
| 2017/0049345 | A1* | 2/2017 | Single .................. A61N 1/0551 |
| 2017/0071490 | A1 | 3/2017 | Parker et al. |
| 2017/0135624 | A1 | 5/2017 | Parker |
| 2017/0173332 | A1 | 6/2017 | Overstreet |
| 2017/0209695 | A1 | 7/2017 | Solomon |
| 2017/0216587 | A1 | 8/2017 | Parker |
| 2017/0216602 | A1 | 8/2017 | Waataja et al. |
| 2017/0296823 | A1 | 10/2017 | Hershey et al. |
| 2017/0361101 | A1 | 12/2017 | Single |
| 2017/0361103 | A1 | 12/2017 | Hadjiyski |
| 2018/0056073 | A1 | 3/2018 | Torgerson |
| 2018/0078769 | A1* | 3/2018 | Dinsmoor .......... A61N 1/36007 |
| 2018/0110987 | A1 | 4/2018 | Parker |
| 2018/0117335 | A1 | 5/2018 | Parker et al. |
| 2018/0126169 | A1 | 5/2018 | Hou et al. |
| 2018/0132760 | A1 | 5/2018 | Parker |
| 2019/0099601 | A1 | 4/2019 | Torgerson |
| 2019/0099602 | A1 | 4/2019 | Esteller et al. |
| 2019/0105496 | A1 | 4/2019 | Min et al. |
| 2019/0209844 | A1 | 7/2019 | Exteller et al. |
| 2019/0388692 | A1 | 12/2019 | Dinsmoor et al. |
| 2019/0388695 | A1 | 12/2019 | Dinsmoor et al. |
| 2020/0038660 | A1* | 2/2020 | Torgerson ........... A61N 1/36164 |
| 2020/0171312 | A1 | 6/2020 | Dinsmoor et al. |

(56) References Cited

U.S. PATENT DOCUMENTS

| | | | |
|---|---|---|---|
| 2020/0171313 | A1 | 6/2020 | Dinsmoor et al. |
| 2020/0305745 | A1* | 10/2020 | Wagenbach ....... A61N 1/36139 |
| 2021/0101007 | A1 | 4/2021 | Hamner et al. |

FOREIGN PATENT DOCUMENTS

| | | | |
|---|---|---|---|
| EP | 3024540 B1 | 10/2018 | |
| WO | 2002009808 A1 | 2/2002 | |
| WO | 2010058178 A1 | 5/2010 | |
| WO | 2012155188 A1 | 11/2012 | |
| WO | 2014210373 A1 | 12/2014 | |
| WO | 2015143509 A1 | 10/2015 | |
| WO | 2015179177 A1 | 11/2015 | |
| WO | 2015179281 A1 | 11/2015 | |
| WO | 2016090420 A1 | 6/2016 | |
| WO | 2016090436 A1 | 6/2016 | |
| WO | 2016191808 A1 | 12/2016 | |
| WO | 2017100866 A1 | 6/2017 | |
| WO | 2017106503 A1 | 6/2017 | |
| WO | 2017173493 A1 | 10/2017 | |
| WO | 2017184238 A1 | 10/2017 | |
| WO | 2017219096 A1 | 12/2017 | |
| WO | 2018080753 A1 | 5/2018 | |
| WO | 2018080754 A1 | 5/2018 | |
| WO | 2018106813 A1 | 6/2018 | |
| WO | 2019231794 A1 | 12/2019 | |

OTHER PUBLICATIONS

Vallejo et al., "Effects of Phase Polarity and Charge Balance Spinal Cord Stimulation on Behavior and Gene Expression in a Rat Model of Neuropathic Pain," Neuromodulation: Technology at the Neural Interface, vol. 23, No. 1, Apr. 2019, 10 pp.

U.S. Appl. No. 17/065,383, by Medtronic, Inc. (Inventors: Dinsmoor et al.), filed Oct. 7, 2020.

U.S. Appl. No. 17/066,219, filed Oct. 8, 2020, naming inventors Dinsmoor et al.

International Search Report and Written Opinion of International Application No. PCT/US2020/055652, dated Jan. 22, 2021, 11 pp.

"St. Jude's Prodigy Neurostimulator with Burst Technology," Medgadget, Mar. 20, 2014, 4 pp.

Abejon MD, "Back pain coverage with spinal cord stimulation: A different treatment for each patient," International Neuromodulation Society. Jun. 10, 2015; 567, Abstract Only, 1 pp.

Abeloos MD, "High density stimulation as an alternative to uncomfortable cervical tonic spinal cord stimulation: case report," International Neuromodulation Society 12th World Congress, Jun. 11-15, 2015, Abstract Only, 1 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD, PhD, et al., "Effect of high-frequency alternating current on spinal afferent nociceptive transmission," Neuromodulation: Technology at the Neural Interface; Jul.-Aug. 2013;16(4): pp. 318-327.

Cui et al., "Spinal cord stimulation attenuates augmented dorsal horn release of excitatory amino acids in mononeuropathy via a GABAergic mechanism," Pain 73, Oct. 1997, pp. 87-95.

Cui, et al., "Effect of spinal cord stimulation on tactile hypersensitivity in mononeuropathic rats is potentiated by simultaneous GABA, sub B. and adenosine receptor activation," Neuroscience Letters 247: Apr. 1998; pp. 183-186.

De Ridder MD, PhD, et al., "Burst spinal cord stimulation: toward paresthesia-free pain suppression," Neurosurgery. May 2010; 66(5): 986-990.

De Ridder, et al., "Burst spinal cord stimulation for limb and back pain," World neurosurgery, Nov. 2013; 80(5):642-649, e641.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res.,1313: (2010) available online Dec. 3, 2009 pp. 53-61.

Grider DO/PhD, et al., "High Frequency (1000 Hz) Stimulation Using Commercially Available Implantable Pulse Generator," North American Neuromodulation Society. Dec. 2013, Abstract Only, 2 pp.

Guan et al., "Spinal Cord Stimulation: Neurophysiological and Neurochemical Mechanisms of Action" Curr Pain Headache Rep DOI 10.1007s11916-014-0260-4, Mar. 8, 2012, pp. 217-225.

Guan MD PhD, et al., "Spinal cord stimulation-induced analgesia: electrical stimulation of dorsal col. and dorsal roots attenuates dorsal horn neuronal excitability in neuropathic rats," Anesthesiology. Dec. 2010;113(6):pp. 1392-1405.

Holsheimer, "Computer modelling of spinal cord stimulation and its contribution to therapeutic efficacy," Spinal Cord Aug. 1998, 36: pp. 531-540.

Hubscher, et al., "Convergence and cross talk in urogenital neural circuitries," J. Neurophysiol 110:1997-2005, first published Aug. 7, 2013, 9 pp.

Hunt SP, Mantyh PW. The molecular dynamics of pain control. Nat Rev Neurosci. Feb. 2001;2(2):83-91.

Kemler MD, et al., "Spinal cord stimulation in patients with chronic reflex sympathetic dystrophy," N Engl J Med, Aug. 31, 2000; 343(9):pp. 618-624.

Kilgore, PhD, et al., "Reversible Nerve Conduction Block Using Kilohertz Frequency Alternating Current," Neuromodulation. Aug. 2013, pp. 242-255.

Kumar, et al., "Spinal cord stimulation versus conventional medical management for neuropathic pain: a multicentre randomised controlled trial in patients with failed back surgery syndrome," Pain Jul. 2007; 132(1-2): 179-188.

Likar et al., "High density spinal cord stimulation: a multi-center experience," Abstracts, International Neuromodulation Society 12th World Congress; Jun. 11-15, 2015, 1 pp.

Maeda, et al., "Increased c-fos immunoreactivity in the spinal cord and brain following spinal cord stimulation is frequency-dependent," Brain Res Mar. 9, 2009;1259: pp. 40-50, available online Jan. 6, 2009.

Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.

Maggi, et al., "Effect of urethane anesthesia on the micturition reflex in capsaicin-treated rats." Journal of the Autonomic Nervous System, Jan. 1990, 30(3): 247-251.

North MD, et al., "Clinical outcomes of 1 kHz subperception spinal cord stimulation (SCS): Results of a prospective andomized controlled crossover trial," Abstracts, International Neuromodulation Society, Jun. 2015, 1 pp.

North MD, et al., "Spinal cord stimulation versus repeated lumbosacral spine surgery for chronic pain: a randomized, controlled trial," Neurosurgery, Jan. 2005; 56(1): 98-106; discussion 106-107.

Ranck Jr., et al., "Which elements are excited in electrical stimulation of mammalian central nervous system: a review," Brain Research, Nov. 21, 1975; 98(3): pp. 417-440.

Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Sato, et al., "Spinal cord stimulation reduces hypersensitivity through activation of opioid receptors in a frequency-dependent manner," Eur J Pain. Apr. 2013 (4): pp. 551-561, first published Oct. 5, 2012.

Schu MD, PhD., et al., "A prospective, randomised, double-blind, placebo-controlled study to examine the effectiveness of burst

(56) References Cited

OTHER PUBLICATIONS spinal cord stimulation patterns for the treatment of failed back surgery syndrome," Meuromodulation. Apr. 2014; 17(5):pp. 443-450.

Shechter MD, et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.

Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.

Smith, et al., "Successful use of high-frequency spinal cord stimulation following traditional treatment failure," Stereotact Funct Neurosurg. Apr. 1, 2015; 93(3): pp. 190-193.

Snellings, et al., "Effects of stimulation site and stimulation parameters on bladder inhibition by electrical nerve stimulation," BJU International, Jul. 2012, pp. 136-143, first published Jan. 19, 2012.

Song MD Phd., et al., "Efficacy of kilohertz-frequency and conventional spinal cord stimulation in rat models of different pain conditions," Neuromodulation Jan. 2014; 17(3): pp. 226-234.

Sweet MD, et al., "High Frequency vs. Burst Stimulation Patterns for Dorsal col. Stimulation: The Importance of Charge," American Association of Neurological Surgeons, Abstract, Apr. 4, 2014, 2 pp.

Walter, et al., "Inhibiting the hyperreflexic bladder with electrical stimulation in a spinal animal model." Neurourology and Urodynamics, 1993, 12:241-253. doi:10.1002/nau.1930120306. Applicant points out in accordance with MPEP 609.04(a) that the 1993 year of publication is sufficiently earlier than the effective U.S. filing date of the present application, and any foreign priority date that the particular month of publication is not in issue.

Wille, MD, et al., "Altering Conventional to High Density Spinal Cord Stimulation: An Energy Dose-Response Relationship in Neuropathic Pain Therapy," Neuromodulation 2016, Aug. 2016, 9 pp.

Woock, et al., "Activation and inhibition of the micturition reflex by penile afferents in the cat," Am J. Physiol Regul Intergre Comp Physiol, published Apr. 23, 2008, pp. R1880-R1889.

Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.

Crosby et al., "Modulation of activity and conduction in single dorsal column axons by kilohertz-frequency spinal cord stimulation," American Physiological Society, published online Oct. 19, 2016, 27 pp.

\* cited by examiner

ECAP SENSING FOR HIGH FREQUENCY NEUROSTIMULATION

This application claims the benefit of U.S. Provisional Application No. 62/926,164, which was filed on Oct. 25, 2019, the entire content of which is incorporated herein by reference.

TECHNICAL FIELD

This disclosure generally relates to medical therapy and, more particularly, electrical stimulation therapy.

BACKGROUND

Medical devices, including implantable medical devices (IMDs), may be used to treat a variety of medical conditions. Medical electrical stimulation devices, for example, may deliver electrical stimulation therapy to a patient via external and/or implanted electrodes. Electrical stimulation therapy may include stimulation of nerve tissue, muscle tissue, the brain, the heart, or other tissue within a patient. In some examples, an electrical stimulation device is fully implanted within the patient. For example, an implantable electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads with percutaneous lead extensions.

Medical electrical stimulators have been proposed for use to relieve a variety of symptoms or conditions such as chronic pain, tremor, Parkinson's disease, depression, epilepsy, migraines, urinary or fecal incontinence, pelvic pain, sexual dysfunction, obesity, and gastroparesis. An electrical stimulator may be configured to deliver electrical stimulation therapy via leads that include electrodes implantable proximate to the spinal cord, pelvic nerves, gastrointestinal organs, sacral nerves, peripheral nerves, or within the brain of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

SUMMARY

In general, the disclosure describes techniques for implementing the use of electrically evoked compound action potentials (ECAPs) to adaptively adjust parameters defining pulses of high frequency electrical stimulation. A characteristic value of a sensed ECAP can be employed to control titration of the amplitude of low frequency spinal cord neurostimulation (SCS) systems so as to maintain a desired level of sensation of paresthesia in the patient. Low frequency stimulation systems typically deliver stimulation pulses having a pulse frequency less than 500 Hertz. However, patients using low frequency systems may experience inconsistent or uneven sensation resulting from subtle shifts in the distance between stimulation electrodes and the spinal cord.

High frequency stimulation typically involves delivery stimulation pulses having a pulse frequency greater than or equal to 500 Hertz. High frequency stimulation potentially employs other mechanisms of action for therapy delivery to the patient as compared to low frequency stimulation. ECAP feedback may still be useful to control parameters of the high frequency stimulation. However, high frequency stimulation pulses may mask ECAPs signals so as to prevent the detection of ECAPs signals from the target nerve. Therefore, techniques for incorporating ECAPs feedback to control low frequency stimulation parameters may be ineffective for deployment in high frequency stimulation systems.

The systems, devices, and techniques disclosed herein provide high frequency stimulation that may also employ ECAPs to adaptively adjust parameters defining the pulses of high frequency electrical stimulation (e.g. stimulation having a pulse frequency greater than or equal to 500 Hertz). In one example, a medical device delivers high frequency stimulation as trains of electrical stimulation pulses with a pause in high frequency electrical stimulation between each train. By temporarily pausing the high frequency stimulation for a predetermined amount of time, the medical device may sense an ECAP response from a target nerve during this amount of time and without interference from delivered pulses. In this manner, the medical device may use the sensed ECAP to adjust values of one or more parameters defining the high frequency stimulation (e.g., for subsequent pulses). In some examples, the last pulse of the train is different from previous pulses in the train and configured to elicit a detectable ECAP. Additionally or alternatively, the medical device may deliver low frequency electrical stimulation during the pause in high frequency stimulation. One or more pulses of the low frequency stimulation may elicit the detectable ECAP signal and/or maintain therapeutic efficacy in the patient during the pause.

Accordingly, by using the techniques described herein, a medical device may pause delivery of high frequency electrical stimulation so as to allow time for the medical device to detect an ECAP signal that can be used to modulate the high frequency electrical stimulation. The ECAP signal may not otherwise be detectable during delivery of pulses because the larger amplitude of delivered pulses from the high frequency electrical stimulation may obscure the ECAP signal. Furthermore, a medical device as described herein may deliver low frequency electrical stimulation while pausing the high frequency electrical stimulation and sensing ECAP signals resulting from one or more pulses of the low frequency stimulation, thereby maintaining therapeutic efficacy in the patient while sensing the ECAP. A medical device as described herein may deliver sufficient pulses for high frequency electrical stimulation while also detecting an ECAP response of the patient during a brief pause in the delivery of pulses, thereby allowing for the use of characteristic values of sensed ECAPs to control titration of values of one or more parameters defining pulses of the high frequency electrical stimulation therapy.

In one example, this disclosure describes a method comprising: delivering, by a medical device, electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, ceasing, by the medical device, the delivery of the electrical stimulation therapy for a predetermined period of time; during the predetermined period of time, sensing, by the medical device, an evoked compound action potential (ECAP) signal from a tissue of the patient; determining, by the medical device and based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, delivering the second train of electrical stimulation pulses according to the value of the at least one parameter at least partially defining the second set of pulses.

In another example, this disclosure describes a medical device configured to: deliver electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, cease the delivery of the electrical stimulation therapy for a predetermined period of time; during the predetermined period of time, sense an evoked compound action potential (ECAP) signal from a tissue of the patient; determine, based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, deliver the second train of electrical stimulation pulses according to the value of the at least one parameter at least partially defining the second set of pulses.

In another example, this disclosure describes a non-transitory, computer-readable medium comprising instructions that, when executed, are configured to cause processing circuitry of an implantable medical device to: control a stimulation generator of the implantable medical device to deliver electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, control the stimulation generator to cease the delivery of the electrical stimulation therapy for a predetermined period of time; during the predetermined period of time, sense an evoked compound action potential (ECAP) signal from a tissue of the patient; determine, based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, control the stimulation generator to deliver the second train of electrical stimulation pulses according to the value of the at least one parameter at least partially defining the second set of pulses.

The details of one or more examples of the techniques of this disclosure are set forth in the accompanying drawings and the description below. Other features, objects, and advantages of the techniques will be apparent from the description and drawings, and from the claims.

BRIEF DESCRIPTION OF DRAWINGS

Like reference characters refer to like elements throughout the figures and description.

DETAILED DESCRIPTION

Figure 1:
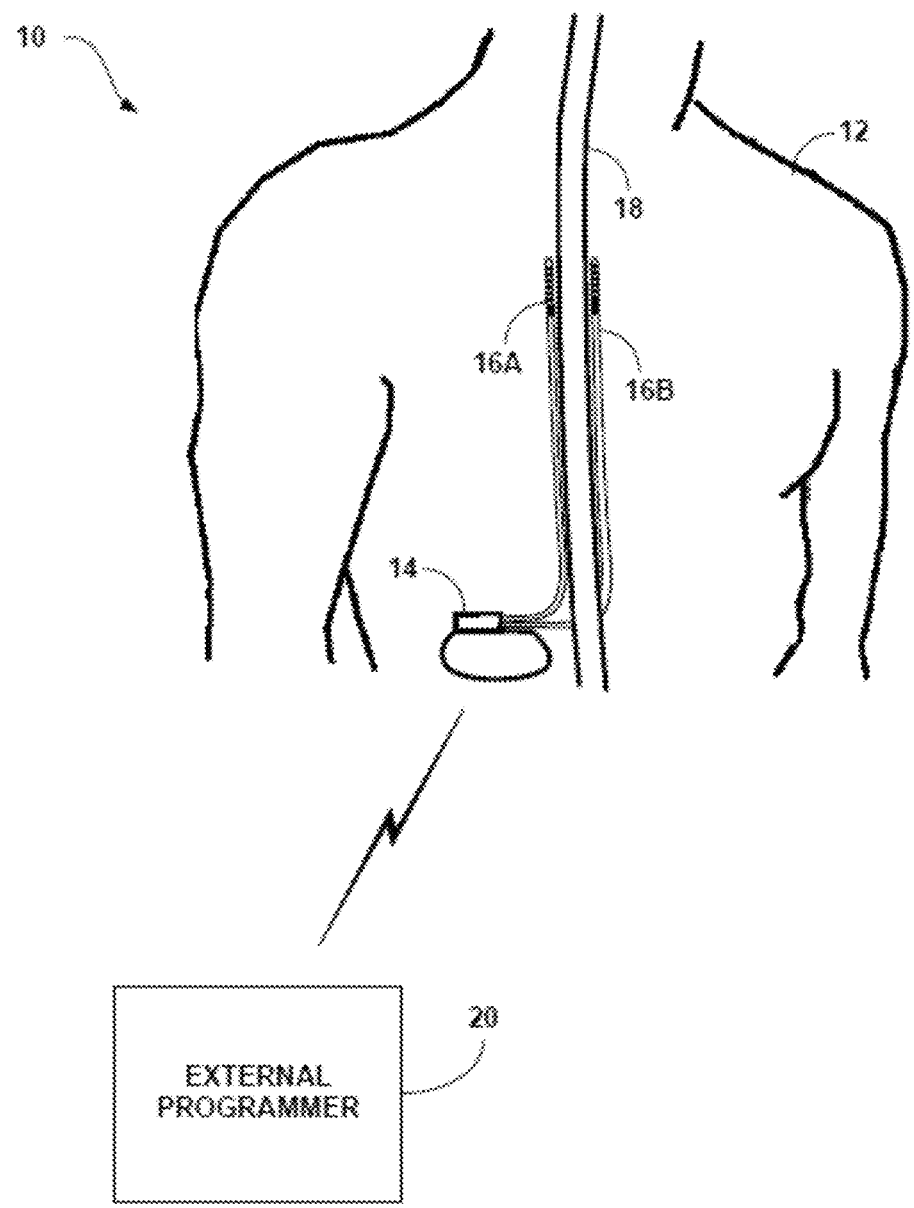
FIG. 1 is a schematic diagram illustrating an example implantable stimulation system including a pair of implantable stimulation electrode arrays carried by implantable leads.

This disclosure includes systems, devices, and methods relating to adjusting electrical stimulation parameter values that define high frequency electrical stimulation delivered to a patient. In therapeutic or intervention type applications, a patient may receive electrical stimulation therapy to relieve a variety of symptoms or conditions. In some cases, a physician or clinician may manually adjust electrical stimulation parameters according to patient feedback, such as the patient's perception on reduction in pain levels or any changes in symptoms. However, patient feedback can be inconsistent over time and is also subjective. In this manner, it may be difficult to determine the most appropriate stimulation parameters to relive the patient's symptoms or conditions and provide improved system performance (e.g., efficient energy usage and targeted therapy delivery).

Spinal cord stimulation (SCS) in patients has historically consisted of low frequency periodic delivery of electrical impulses to the dorsal column of the patient for the purpose of inducing paresthesia. As described herein, "low frequency electrical simulation" refers to electrical stimulation comprising a pulse frequency less than 500 Hertz that may generally produce paresthesia for the patient. The paresthesia serves to mask pain felt in specific regions of the body, such as the lower back or legs. Sensory signals, in this case, the periodic electrical impulses from the spinal cord stimulator or the pain signal itself, are relayed to the brain via the dorsal columns of the spinal cord. The dorsal column consists of multiple sensory nerve fiber types, categorized generally by the fiber thickness and their associated signal propagation velocities. Very thick (13-20 μm) Aα fibers have action potential propagation velocities around 100 m/s and are associated with proprioception. Thick diameter (6-12 μm) Aβ fibers are heavily myelinated with action potential propagation velocities approaching 60 m/s. Paresthesia with SCS is thought to result from modulation of Aβ fibers. Thinner diameter (2-5 μm), myelinated Aδ fibers have action potential propagation velocities on the order of 10 m/s. Unmyelinated C fibers (0.2 μm-1.5 μm) transmit signals at 2 m/s. Both Aδ and C fibers are responsible for transmitting pain signals to the brain, with Aδ and C fibers contributing acute and burning pain characteristics, respectively.

There are a number of factors which may affect the propagation of signals along the spinal cord. Examples include the presence or absence of certain chemical factors, disease state, or electrical stimulation. In some instances, it is desirable to adapt a therapeutic intervention with a patient based on the measured signal propagation characteristics of the spinal cord. One method for dealing with these factors that may change over time involves detecting the ECAP signal. In various examples, an electrical stimulus is applied to the spinal cord of a patient at a particular location, and the resultant ECAP can be detected and recorded. The sensing and measurement of these ECAP signals are not limited to the spinal cord, and may also be recorded in other locations besides the spinal cord, such as peripheral nerves, or for example from within the brain.

In view of these factors, other parameters for delivery of SCS therapies that are different from the historically applied SCS therapies may provide efficacy in treatment for a particular patient. For example, SCS systems which deliver stimulation at a high frequency utilize a much faster pulse frequency than traditional SCS therapies provided at, e.g., a 50 Hertz frequency. As described herein, "high frequency electrical simulation" refers to electrical stimulation comprising a pulse frequency greater than or equal to 500 Hertz. The asserted advantage of the application of high frequency electrical stimulation therapy is that patients have reported a reduction or elimination of the pain sensation(s) without the associated paresthesia sensation typically experienced when using low frequency SCS therapies. However, at least one drawback to these high frequency pulses is that the electrical pulse trains delivered to the patient at high frequency may mask any ECAP signal. Therefore, while a medical device delivers high frequency electrical stimulation to the patient, the medical device may be unable to detect an ECAP, preventing the medical device from using the ECAP response to control titration of values of one or more parameters that define the pulses of the high frequency electrical stimulation.

As discussed herein, systems, devices, and methods are described for adjusting one or more parameters of high frequency electrical stimulation based on a detected ECAP. The ECAP may be evoked in response to the application of one or more electrical stimulation pulses that is defined according to a set of stimulation parameters. Adjustments to the electrical stimulation parameters based on the detected ECAP may provide more objective information than patient feedback. In addition, ECAP detection may allow a system to provide closed-loop stimulation control. Incorporation of ECAP into adjustment, and/or titration, of stimulation parameters may enable stimulation systems to provide stimulation therapy that uses less energy, improved patient perception of the stimulation, more targeted stimulation delivery to desired tissues, and/or improved therapeutic efficacy as compared to techniques that do not incorporate ECAP detection. In some examples, dorsal column stimulation therapy (e.g., a type of spinal cord stimulation) or other electrical stimulation therapy is provided according to a therapy program defining values for stimulation parameters, such as current or voltage amplitude, pulse frequency, pulse width, burst frequency, and/or pulse shape that are selected to provide a level of therapy, such as a reduction in, or elimination of, pain felt by the patient. Spinal cord stimulation may also include stimulation of dorsal nerve roots in some examples. Further, stimulation is not limited to stimulation of the spinal cord, and may be applied to peripheral nerves or their end organs. Further, peripheral stimulators do not have to be implanted devices, and they may also comprise non-electrical stimuli (e.g., mechanical, thermal).

The techniques, systems, and devices disclosed herein can provide high frequency stimulation employing ECAPs to adaptively adjust parameters that define the high frequency electrical stimulation (e.g. stimulation having a pulse frequency greater than or equal to 500 Hertz). In one example, a medical device delivers high frequency stimulation as trains of electrical stimulation pulses with a pause in high frequency electrical stimulation between each train. By temporarily pausing the high frequency stimulation for a predetermined amount of time, the medical device may sense an ECAP response from a target nerve during this amount of time, thereby allowing the medical device to use the sensed ECAP to adjust a value of the one or more parameters defining pulses of the high frequency stimulation. In some examples, the medical device uses a last pulse of the train that is different from the other pulses of the train and configured to elicit a detectable ECAP. Additionally or alternatively, the medical device may deliver low frequency electrical stimulation (e.g., one or more pulses) during the pause in high frequency stimulation so as to elicit the ECAP response and/or maintain therapeutic efficacy in the patient during the pause. Accordingly, by using the techniques described herein, a medical device may be enabled to deliver high frequency electrical stimulation and sense an ECAP response during a pause in high frequency stimulation such that the device can use ECAP signal as feedback to modulate one or more parameters of the high frequency electrical stimulation for subsequent delivery. Without such a pause in delivery of the high frequency electrical stimulation, the ECAP signal may not be detectable and used for feedback.

The detected ECAP may provide more objective information, as compared with patient feedback, for adjusting parameter values that define subsequent high frequency stimulation pulses. In addition, the techniques set forth herein enable a device to employ ECAP detection as a closed-loop control for a system that delivers high frequency electrical stimulation. By incorporating the detection of ECAP signals into feedback for adjusting stimulation parameters, and/or titration, a medical device may deliver high frequency electrical stimulation providing more targeted stimulation delivery to desired tissues, improved therapeutic efficacy, and/or less power consumption, as compared to techniques that do not incorporate ECAP detection. An electrical sensing system, such as one within an implantable medical device, or in electrical communication with such an implantable medical device, may perform the ECAP detection described herein. The sensing system may include one or more electrodes positioned at some distance away from the site of the application of the electrical stimulation.

In some examples, detection, or the lack thereof, of the presence of the ECAP in response to stimulation provided at a particular set of therapy parameters is used to program initial stimulation therapy parameters provided to a patient via an implantable medical device. In other examples, the detection of ECAP in response to stimulation provided at a particular set of therapy parameters may be used to automatically adjust existing stimulation therapy parameters. The presence or absence of an ECAP or a characteristic value of the ECAP in response to a set of stimulation therapy program may be used to control programing and adjustment of parameters of high frequency electrical stimulation.

For example, an IMD (or other medical device) may start providing stimulation according to an initial therapy parameter set, e.g., including a relatively high frequency, such as 15 kHz. The IMD detects an ECAP signal that is generated by one or more nerve fibers as a result of the applied stimulation and compares a characteristic value of the ECAP signal to a target characteristic value for the ECAP. Based on the comparison, the IMD may adjust one or more parameters of the stimulation therapy so as to reduce the difference between the characteristic value of the ECAP signal and the target characteristic value for the ECAP. For example, the IMD may lower the amplitude and/or pulse frequency of the applied stimulation pulses to generate a new set of therapy parameters for subsequent therapy. The IMD may then apply the new stimulation therapy to the patient, sense the resulting ECAP generated as a result of the application of the new therapy, and may further generate a new set of therapy parameters for the therapy, in accordance with this closed loop control scheme.

In some examples, a given stimulation therapy may be applied to a patient, and the resulting ECAP signal sensed and analyzed to determine whether the patient's response to that same particular set of stimulation parameters has changed. In some examples, detection of the ECAP signal in response to a current stimulation therapy program is performed on an ongoing basis. For example, ECAP signal may be detected every few seconds, once a minute, once every few minutes, hourly, daily or weekly. In some examples, the medical device may elicit and detect an ECAP signal in response to a change in another sensed physiological parameter. For example, the medical device may pause high frequency stimulation to detect an ECAP signal when there has been a change in activity level or posture of the patient that may indicate a value of one or more parameters of the high frequency stimulation pulses should be changed (e.g., because the electrodes may have moved with respect to a target nerve). These changes in activity level and/or posture of a patient may be sensed and/or determined by a same device providing the stimulation therapy to the patient or by devices that are not the same devices providing the stimulation therapy to the patient.

A patient as used herein in general refers to a human patient, but is not limited to humans, and may include animals. Various references to a "test patient" as used herein may include animals used to receive test stimulation patterns and to collect data related to the stimulation tests according to the various techniques described herein.

FIG. 1 is a schematic diagram illustrating an example implantable stimulation system 10 including a pair of implantable electrode arrays in the form of stimulation leads 16A and 16B. Although the techniques described in this disclosure may be generally applicable to a variety of medical devices including external and implantable medical devices (IMDs), application of such techniques to IMDs and, more particularly, implantable electrical stimulators such as neurostimulators will be described for purposes of illustration. More particularly, the disclosure will refer to an implantable spinal cord stimulation (SCS) system for purposes of illustration, but without limitation as to other types of medical devices.

As shown in FIG. 1, system 10 includes an IMD 14 and external programmer 20 shown in conjunction with a patient 12. In the example of FIG. 1, IMD 14 is an implantable electrical stimulator configured for spinal cord stimulation (SCS), e.g., for relief of chronic pain or other symptoms. Again, although FIG. 1 shows an implantable medical device, other embodiments may include an external stimulator, e.g., with percutaneously implanted leads, or implanted leads with percutaneous lead extensions. Stimulation energy is delivered from IMD 14 to spinal cord 18 of patient 12 via one or more electrodes disposed on implantable leads 16A and 16B (collectively "leads 16"). In some applications, such as spinal cord stimulation (SCS) to treat chronic pain, the adjacent implantable leads 16 may have longitudinal axes that are substantially parallel to one another.

Although FIG. 1 is directed to SCS therapy, system 10 may alternatively be directed to any other condition that may benefit from stimulation therapy. For example, system 10 may be used to deliver stimulation to one or more tissues in order to treat tremor, Parkinson's disease, epilepsy, urinary or fecal incontinence, sexual dysfunction, obesity, or gastroparesis. In this manner, system 10 may be configured to provide therapy taking the form of deep brain stimulation (DBS), pelvic floor stimulation, gastric stimulation, or any other stimulation therapy. In addition, patient 12 is ordinarily a human patient.

Each of leads 16 may include electrodes and the parameters for a program that controls delivery of stimulation therapy by IMD 14 may include information identifying which electrodes have been selected for delivery of stimulation according to a stimulation program, the polarities of the selected electrodes, i.e., the electrode configuration for the program, and voltage or current amplitude, pulse rate, and pulse width of stimulation delivered by the electrodes. Delivery of stimulation pulses will be described for purposes of illustration. However, stimulation may be delivered in other forms such as continuous waveforms. Programs that control delivery of other therapies by IMD 14 may include other parameters, e.g., such as dosage amount, rate, or the like for drug delivery.

In the example of FIG. 1, leads 16 carry one or more electrodes that are placed adjacent to the target tissue of the spinal cord. One or more electrodes may be disposed at a distal tip of a lead 16 and/or at other positions at intermediate points along the lead. Leads 16 may be implanted and coupled to IMD 14. Alternatively, as mentioned above, leads 16 may be implanted and coupled to an external stimulator, e.g., through a percutaneous port. In some cases, an external stimulator may be a trial or screening stimulation that used on a temporary basis to evaluate potential efficacy to aid in consideration of chronic implantation for a patient. In additional embodiments, IMD 14 may be a leadless stimulator with one or more arrays of electrodes arranged on a housing of the stimulator rather than leads that extend from the housing.

The stimulation may be delivered via selected combinations of electrodes carried by one or both of leads 16, e.g., in bipolar, unipolar, or multipolar combinations. The target tissue may be any tissue affected by electrical stimulation energy, such as electrical stimulation pulses or waveforms. Such tissue includes nerves, smooth muscle, and skeletal muscle. In the example illustrated by FIG. 1, the target tissue is spinal cord 18. Stimulation of spinal cord 18 may, for example, prevent pain signals from traveling through the spinal cord and to the brain of the patient. Patient 12 may perceive the interruption of pain signals as a reduction in pain and, therefore, efficacious therapy results.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which multiplexing operations may be applied. Such electrodes may be arranged as surface electrodes, ring electrodes, or protrusions. As a further alternative, electrode arrays may be formed by rows and/or columns of electrodes on one or more paddle leads. In some embodiments, electrode arrays may include electrode segments, which may be arranged at respective positions around a periphery of a lead, e.g., arranged in the form of one or more segmented rings around a circumference of a cylindrical lead. Other electrode and lead configurations may be adapted for use with the present disclosure so long as they enable IMD 14 to electrically stimulate and sense from a target tissue.

In the example of FIG. 1, stimulation energy is delivered by IMD 14 to the spinal cord 18 to reduce the amount of pain perceived by patient 12. As described above, IMD 14 may be used with a variety of different pain therapies, such as peripheral nerve stimulation (PNS), peripheral nerve field stimulation (PNFS), DBS, cortical stimulation (CS), sacral neuromodulation (SNM), pelvic floor stimulation, gastric stimulation, and the like. The electrical stimulation delivered by IMD 14 may take the form of electrical stimulation pulses or continuous stimulation waveforms, and may be characterized by controlled voltage levels or controlled current levels, as well as pulse width and pulse rate (i.e., pulse frequency) in the case of stimulation pulses.

In some examples, IMD 14 may deliver stimulation therapy according to one or more programs. A program defines one or more parameters that define an aspect of the therapy delivered by IMD 14 according to that program. For example, a program that controls delivery of stimulation by IMD 14 in the form of pulses may define a voltage or current pulse amplitude, a pulse width, and a pulse rate, for stimulation pulses delivered by IMD 14 according to that program. The program may also define an electrode combination for delivery of the stimulation pulse, including electrode polarities. Moreover, therapy may be delivered according to multiple programs, wherein multiple programs are contained within each of a multiple of groups.

During use of IMD 14 to treat patient 12, movement of patient 12 among different posture states may affect the ability of IMD 14 to deliver consistent efficacious or optimally perceived therapy. For example, leads 16 may migrate toward IMD 14 when patient 12 bends over, resulting in displacement of electrodes and possible disruption in delivery of effective therapy. Stimulation energy transferred to target tissue may be reduced due to electrode motion, causing reduced efficacy in terms of relief of symptoms such as pain. As another example, leads 16 may be compressed towards spinal cord 18 when patient 12 lies down. Such compression may cause an increase in the amount of stimulation energy transferred to target tissue. In this case, the amplitude of stimulation therapy may be decreased to avoid causing patient 12 additional pain or unusual sensations, which may be considered undesirable side effects that undermine overall efficacy.

Also, posture state changes may present changes in symptoms or symptom levels, e.g., pain level. Reduced efficacy due to increased coupling or decreased coupling of stimulation energy to target tissue may occur due to changes in posture and/or activity level associated with patient posture state. To avoid or reduce possible disruptions in effective therapy due to posture state changes, IMD 14 may include a posture state module that detects the posture state of patient 12 and causes the IMD 14 to automatically detect an ECAP signal in response to a change in posture state. Based on the detected ECAP signal, IMD 14 determines whether an adjustment to the stimulation parameters is recommended or otherwise appropriate. For example, a posture state module may include a posture state sensor, such as an accelerometer, that detects when patient 12 lies down, stands up, or otherwise changes posture. In some examples, the posture state detected by the posture state sensor may also include a level of activity instead of, or in addition to, the posture of the patient.

A posture state module may include, for example, one or more accelerometers that detect when patient 12 occupies a posture state in which it may be appropriate to decrease the stimulation amplitude, e.g., when patient 12 lies down. In some examples, the IMD may automatically reduce stimulation amplitude so that patient 12 does not manually have to do so. The IMD may then detect an ECAP signal in response to the adjusted stimulation parameters to determine if the adjustment was effective. In other examples, the IMD may detect an ECAP signal in response to stimulation when a change in posture is detected prior to making an adjustment to the stimulation parameters. IMD 14 may analyze the detected ECAP signal to determine one or more characteristic values of the ECAP signal (e.g. an amplitude of or between one or more peaks of the detected ECAP or an area under the curve of one or more peaks of the ECAP) and then determine the appropriate adjustment to one or more values of the stimulation parameters. Example posture states may include "Upright," "Upright and Active," "Lying Down," and so forth.

As will be described in greater detail below, in some examples, IMD 14 may be configured to automatically adjust stimulation amplitude when it detects that patient 12 has changed position. In some examples, in response to detection of a change in position, IMD 14 determines an appropriate adjustment to the stimulation parameters. In some examples, the determination may include detecting ECAP signals based on the current stimulation parameters, and making adjustments to one or more stimulation parameters based on the determined characteristic value of the ECAP signal detected. In other examples, IMD 14 may select a new set of stimulation parameters stored in a memory based on previously detected ECAP for the same position.

In some examples, stimulation parameter may be configured to be changed at a rate suitable to prevent undesirable effects, e.g., such as the effects due to the compression of leads 16 towards spinal cord 18 when patient 12 lies down. In some examples, IMD 14 may be configured to decrease the stimulation amplitude to a first predetermined lower amplitude value substantially immediately upon detection by IMD 14 that patient 12 is lying down. IMD 14 may then evaluate the appropriateness of the new stimulation amplitude based on ECAP, and make further adjustments as necessary. In other examples, IMD 14 may be configured to detect an ECAP signal to stimulation upon detection of patient 12 lying down. Based on the detected ECAP signal, IMD 14 may adjust one or more stimulation parameters until a desired characteristic of the detected ECAP signal is achieved.

In response to a posture state indication by the posture state module, IMD 14 may change a program group, program, stimulation amplitude, pulse width, pulse rate, and/or one or more other parameters, groups or programs to maintain therapeutic efficacy. When a patient lies down, for example, IMD 14 may automatically reduce stimulation amplitude so that patient 12 does not need to reduce stimulation amplitude manually. The amount of automatic reduction may be determined, at least in part, based on the characteristic value of the detected ECAP signal in the new posture state. In some cases, IMD 14 may communicate with external programmer 20 to present a proposed change in stimulation in response to a posture state change, for example for a first posture state to a second posture state, and receive approval or rejection of the change from a user, such as patient 12 or a clinician, before automatically applying the therapy change. In some examples, posture state detection may also be used to provide notifications, such as providing notification via a wireless link to a care giver that a patient has potentially experienced a fall.

In some examples, IMD 14 may periodically detect ECAPs generated in response to current stimulation parameters and adjust the current stimulation parameters if there has been a significant change, i.e., greater than a predetermined threshold change, to a characteristic value of the detected ECAP signal relative to a target ECAP characteristic value. IMD 14 may detect and analyze ECAPs on an hourly, daily, weekly, or monthly basis for example. In some examples, IMD 14 may initiate an ECAP signal detection and analysis cycle if a predetermined amount of time has passed since the last ECAP detection. IMD 14 may reset this time in response to detecting an ECAP signal. In some examples, IMD 14 may adjust a rate of ECAP detection based on a posture of patient 12 or in response to a change in posture of patient 12. For example, in response to detecting that patient 12 has changed posture, IMD 14 may increase or decrease a rate at which ECAPs are detected.

A user, such as a clinician or patient 12, may interact with a user interface of external programmer 20 to program IMD 14. The user interface may include an output device for presentation of information, and an input device to receive user input. Programming of IMD 14 may refer generally to the generation and transfer of commands, programs, or other information to control the operation of IMD 14. For example, external programmer 20 may transmit programs, parameter adjustments, program selections, group selections, or other information to control the operation of IMD 14, e.g., by wireless telemetry. As one example, external programmer 20 may transmit parameter adjustments to support therapy changes due to posture changes by patient 12. As another example, a user may select programs or program groups. Again, a program may be characterized by an electrode combination, electrode polarities, voltage or current amplitude, pulse width, pulse rate, and/or duration. A program group may be characterized by multiple programs that are delivered simultaneously or on an interleaved or rotating basis.

During the delivery of stimulation therapy, patient 12 may make patient therapy adjustments, i.e., patient adjustments to one or more parameters of a therapy via an input device of a user interface of a programmer, to customize the therapy either after patient 12 moves to a different posture state or in anticipation of the next posture state. As described in more detail below, IMD 14 may detect an ECAP in response to the therapy adjustment. In some examples, the detected ECAP in response to the adjusted therapy may be stored as indicating effective therapy for a particular patient state. If the same patient state is detected again, IMD 14 may automatically adjust one or more stimulation parameters in order to achieve a characteristic value of the ECAP which corresponds to the stored target ECAP characteristic value. In examples where IMD 14 is in a record mode to store all patient therapy adjustments associated with a specific patient state, IMD 14 may implement a method to ensure that patient therapy adjustments are associated with the correct patient state intended by patient 12 when the therapy adjustment was made. The patient 12 may occupy the patient state multiple times such that there are multiple instances of the sensed patient state. A patient state may be a posture or activity level, for example. In some examples, each time the patient 12 occupies a posture state, the patient may enter one or more therapy adjustments.

In some cases, external programmer 20 may be characterized as a physician or clinician programmer if it is primarily intended for use by a physician or clinician. In other cases, external programmer 20 may be characterized as a patient programmer if it is primarily intended for use by a patient, e.g., for entry of patient input to specify patient adjustments to one or more therapy parameters. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use, either manually or via other user input media.

IMD 14 may be constructed with a biocompatible housing, such as titanium or stainless steel, or a polymeric material such as silicone or polyurethane, and surgically implanted at a site in patient 12 near the pelvis. IMD 14 may also be implanted in patient 12 at a location minimally noticeable to patient 12. Alternatively, IMD 14 may be external with percutaneously implanted leads. For SCS, IMD 14 may be located in the lower abdomen, lower back, upper buttocks, or other location to secure IMD 14. Leads 16 may be tunneled from IMD 14 through tissue to reach the target tissue adjacent to spinal cord 18 for stimulation delivery.

At the distal ends of leads 16 are one or more electrodes that transfer the electrical stimulation from the lead to the tissue. The electrodes may be electrode pads on a paddle lead, circular (e.g., ring) electrodes surrounding the body of leads 16, conformable electrodes, cuff electrodes, segmented electrodes (e.g., partial ring electrodes located at different circumferential positions around the perimeter of the lead), or any other type of electrodes capable of forming unipolar, bipolar or multipolar electrode configurations for therapy. The electrodes may pierce or affix directly to the tissue itself. In general, ring electrodes arranged at different axial positions at the distal ends of leads 16 will be described for purposes of illustration.

One or more characteristic values of ECAPs are employed to control titration of the amplitude of low frequency SCS systems so as to maintain a sensation of even paresthesia in patient 12. Low frequency stimulation typically includes stimulation pulses having a pulse frequency less than 500 Hertz. However, patients using low frequency stimulation may experience inconsistent or uneven sensation resulting from subtle shifts in the stimulation electrodes with respect to the spinal cord. High frequency stimulation typically includes stimulation pulses having a pulse frequency greater than or equal to 500 Hertz. High frequency stimulation may potentially employ other mechanisms of action such that the patient may experience a reduction in pain instead of paresthesia (or with a lower level of paresthesia). High frequency stimulation efficacy may also change as the patient moves. However, high frequency stimulation pulses may occur too frequently such that the presence of these delivered pulses mask ECAPs signals so as to prevent detection of ECAPs signals from the target nerve. Therefore, techniques for incorporating ECAPs feedback to control, or modulate, high frequency stimulation pulses (and low frequency stimulation parameters in some examples) may include pauses during delivery of the high frequency stimulation for a predetermined period of time long enough to detect at least one ECAP signal.

In accordance with the techniques of the disclosure, IMD 14 may use ECAPs to adaptively determine (e.g., set or adjust) parameters of high frequency electrical stimulation. In one example, IMD 14 delivers high frequency stimulation as trains of electrical stimulation pulses with a pause in high frequency electrical stimulation between each train. By temporarily pausing the high frequency stimulation for a predetermined amount of time, IMD 14 may sense an ECAP signal from a target nerve (or nerves) of patient 12 during this amount of time without interference from the high frequency stimulation. Therefore, IMD 14 may use the sensed ECAP to adjust the parameters of the high frequency stimulation. In some examples, IMD 14 delivers the last pulse of the train (e.g., a master pulse) to elicit a detectable ECAP, where the last pulse is different than previous pulses (e.g., primary pulses) within the same train. Additionally or alternatively, IMD 14 may deliver low frequency electrical stimulation during the pause in high frequency stimulation so as to elicit the ECAP response and/or maintain therapeutic efficacy in patient 12 during the pause.

Accordingly, by using the techniques described herein, IMD 14 may pause delivery of high frequency electrical stimulation so as to allow time for IMD 14 to detect an ECAP response to the high frequency electrical stimulation, the ECAP which may otherwise not be detectable by other systems that deliver continuous high frequency electrical stimulation. Furthermore, a medical device as described herein may deliver low frequency electrical stimulation while pausing the high frequency electrical stimulation and sensing the ECAP, thereby maintaining therapeutic efficacy in patient 12 while sensing the ECAP. Therefore, a medical device as described herein may avoid masking an ECAP signal of the patient with one or more pulses of high frequency electrical stimulation, thereby allowing for the use of sensed ECAPs as control signals for titrating one or more parameters of the high frequency electrical stimulation therapy.

Figure 2:
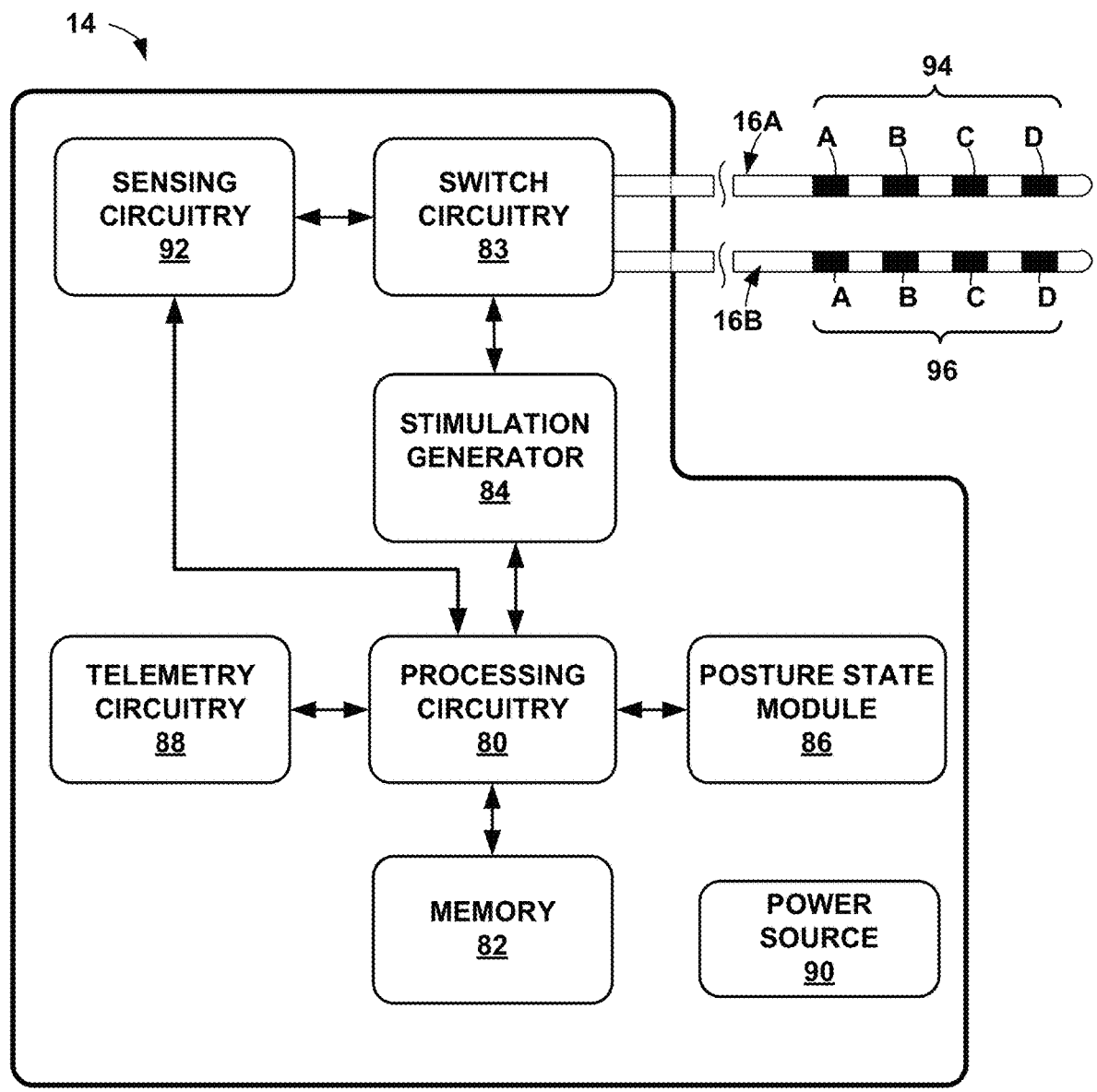
FIG. 2 is a functional block diagram illustrating example components of an IMD, such as the IMD shown in FIG. 1.

FIG. 2 is a functional block diagram illustrating various components of an IMD 14. In the example of FIG. 2, IMD 14 includes a processing circuitry 80, memory 82, switch circuitry 83, stimulation generator 84, posture state module 86, telemetry circuit 88, power source 90, and sensing circuitry 92. The stimulation generator 84 may form a therapy delivery module. Processing circuitry 83 may control switch circuitry 83 which switches signals to and/or from leads 16 to sensing circuitry 92 and/or stimulation generator 84. Memory 82 may store instructions for execution by processing circuitry 80, stimulation therapy data, ECAP characteristic values, posture state information, posture state indications, and any other information regarding therapy or patient 12. Therapy information may be recorded for long-term storage and retrieval by a user, and the therapy information may include any data created by or stored in IMD 14. Memory 82 may include separate memories for storing instructions including instructions for ECAP analysis, posture state information, therapy adjustment information, prior detected ECAP signals and/or characteristic values of ECAPs, program histories, and any other pertinent data or instructions.

Processing circuitry 80 controls stimulation generator 84 to deliver electrical stimulation via electrode combinations formed by electrodes in one or more electrode arrays. For example, stimulation generator 84 may deliver electrical stimulation therapy via electrodes (e.g., electrodes 94A-94D and 96A-86D of respective leads 16A and 16B) on one or more leads 16, e.g., as stimulation pulses or continuous waveforms. Components described as processing circuitry within IMD 14, external programmer 20 or any other device described in this disclosure may each comprise one or more processors, such as one or more microprocessors, digital signal processors (DSPs), application specific integrated circuits (ASICs), field programmable gate arrays (FPGAs), programmable logic circuitry, or the like, either alone or in any suitable combination.

Stimulation generator 84 may include stimulation generation circuitry to generate stimulation pulses or waveforms and switching circuitry to switch the stimulation across different electrode combinations, e.g., in response to control by processing circuitry 80. In particular, processing circuitry 80 may control the switching circuitry on a selective basis to cause stimulation generator 84 to deliver electrical stimulation to selected electrode combinations and to shift the electrical stimulation to different electrode combinations in a first direction or a second direction when the therapy must be delivered to a different location within patient 12. In other examples, stimulation generator 84 may include multiple current sources and sinks to drive more than one electrode combination at one time. For example, each electrode may have its own current source and current sink, which can be selectively activated so that the electrode can source or sink controlled amounts of current. An electrode configuration, e.g., electrode combination and associated electrode polarities, may be represented by a data stored in a memory location, e.g., in memory 82, of IMD 14. Processing circuitry 80 may access the memory location to determine the electrode combination and control stimulation generator 84 to deliver electrical stimulation via the indicated electrode combination. To adjust electrode combinations, amplitudes, pulse rates, or pulse widths, processing circuitry 80 may command stimulation generator 84 to make the appropriate changes to therapy according to instructions within memory 82 and rewrite the memory location to indicate the changed therapy. In other examples, rather than rewriting a single memory location, processing circuitry 80 may make use of two or more memory locations.

When activating stimulation, processing circuitry 80 may access not only the memory location specifying the electrode combination but also other memory locations specifying various stimulation parameters such as voltage or current amplitude, pulse width and pulse rate. Stimulation generator 84, e.g., under control of processing circuitry 80, then makes use of the electrode combination and parameters in formulating and delivering the electrical stimulation to patient 12.

According to examples described herein, processing circuitry 80 may adjust such stimulation parameters to modify stimulation therapy delivered by IMD 14 based on the detected ECAP signal of patient 12. In some examples, processing circuitry 80 may detect an ECAP signal of patient 12 via sensing circuitry 92 that indicates that a modification of the stimulation therapy is appropriate, e.g., according to instructions stored in memory 82. Processing circuitry 80 may access instructions for modifying the stimulation therapy based on the detected ECAP signal, e.g., by changing from the current stimulation program to a program which results in a desired characteristic value of the ECAP (e.g., a characteristic value that achieves a target ECAP characteristic value).

According to other examples described herein, such stimulation parameters may be adjusted to modify stimulation therapy delivered by IMD 14 based on a combination of the detected ECAP signal and a detected posture state. In some examples, processing circuitry 80 may detect an ECAP signal of patient 12 via sensing circuitry 92 as well as a posture state of patient 12 via posture state module 86. If a change in ECAP signal (e.g., a change in a characteristic value of the ECAP) has been detected, a detected posture state may be used to help processing circuitry 80 determine the appropriate stimulation program in order to achieve a target ECAP characteristic value. For example, memory 82 may include a stimulation program associated with the detected posture state which resulted in the target ECAP characteristic value in the past.

Processing circuitry 80 accesses stimulation parameters in memory 82, e.g., as programs and groups of programs. Upon selection of a particular program group, processing circuitry 80 may control stimulation generator 84 to deliver stimulation according to the programs in the groups, e.g., simultaneously or on a time-interleaved basis. A group may include a single program or multiple programs. As mentioned previously, each program may specify a set of stimulation parameters, such as amplitude, pulse width and pulse rate. In addition, each program may specify a particular electrode combination for delivery of stimulation. Again, the electrode combination may specify particular electrodes in a single array or multiple arrays, e.g., on a single lead or among multiple leads. Processing circuitry 80 also may control telemetry circuit 88 to send and receive information to and from external programmer 20. For example, telemetry circuit 88 may send information to and receive information from programmer 20.

In some examples, IMD 14 includes a posture state module 86 which allows IMD 14 to sense or detect the current patient posture state, e.g., posture, activity or any other static position or motion of patient 12. In the example of FIG. 2, posture state module 86 may include one or more accelerometers, such as three-axis accelerometers, capable of detecting static orientation or vectors in three-dimensions. The three-axis accelerometer may be a micro-electro-mechanical accelerometer. In other examples, posture state module 86 may alternatively or additionally include one or more gyroscopes, pressure transducers or other sensors to sense the current posture state occupied by patient 12. Posture state information generated by posture state module 86 and processing circuitry 80 may correspond to an activity and/or posture undertaken by patient 12 or a gross level of physical activity, e.g., activity counts based on footfalls or the like.

Posture state information from posture state module 86 may be stored in memory 82 for later review by a clinician, used to adjust therapy, present a posture state indication to patient 12 and/or clinician, e.g., via user interface display of external programmer 20, or some combination thereof. As an example, processing circuitry 80 may record the posture state parameter value, or output, of the 3-axis accelerometer and assign the posture state parameter value to a certain predefined posture indicated by the posture state parameter value. In this manner, IMD 14 may be able to track how often patient 12 remains within a certain posture state. IMD 14 may also store which group or program was being used to deliver therapy when patient 12 was in the sensed posture state. Further, processing circuitry 80 may also adjust therapy for a new posture state when posture state module 86 indicates that patient 12 has in fact changed postures. In some examples, the change in posture may trigger sensing of ECAP signals. Based on the sensed ECAP from sensing circuitry 92, processing circuitry 80 may determine an appropriate adjustment to one or more current stimulation therapy parameters in order to achieve a target ECAP characteristic value. In some examples, a current characteristic value of the ECAP signal may be compared to a target ECAP characteristic value (e.g., a numerical value for a characteristic or an ECAP signal template) corresponding to efficacious therapy.

Processing circuitry 80 may analyze the sensed ECAP signal to determine values of different types of characteristics in accordance with the techniques described herein. For example, a sensed ECAP signal may include a first peak amplitude, a second peak amplitude, and a third peak amplitude representative of propagating action potentials from the ECAP. The example duration of each peak is approximately 1 millisecond (ms). As one example, the characteristic of the ECAP may be the amplitude between the first and second peaks. This amplitude may be easily detectable even in the presence of artifacts or electronic drift in the sensed signal. In other examples, the characteristic may be an amplitude of one of the first, second, or third peaks with respect to neutral or zero voltage. In some examples, the characteristic may be a sum of two or more of the first, second, or third peaks. In other examples, the characteristic may be the area under one or more of the first, second, or third peaks. In other examples, the characteristic of the ECAP may be a ratio of one of the first, second, or third peaks to another one of the peaks. In some examples, the characteristic of the ECAP may be a slope between two points in the ECAP signal, such as a slope between two of the first, second, or third peaks. In other examples, the characteristic of the ECAP may be the time between two points of the ECAP, such as a time between two of the first, second, or third peaks. The time between when a stimulation pulse is delivered and a point in the ECAP signal may be referred to as a latency of the ECAP and may indicate the types of fibers being captured by the control stimulation pulse. The latency of the ECAP may also be a characteristic evaluated by processing circuitry 80. ECAP signals with lower latency (e.g., smaller latency values) indicate a higher percentage of nerve fibers that have faster propagation of signals, whereas ECAP signals with higher latency (e.g., larger latency values) indicate a higher percentage of nerve fibers that have slower propagation of signals. Other characteristics of the ECAP signal may be used in other examples.

The amplitude of the ECAP signal increases with increased amplitude of the stimulation pulse, as long as the pulse amplitude is greater than a threshold such that nerves depolarize and propagate the signal. A target ECAP characteristic (e.g., a target ECAP amplitude) may be determined from the ECAP signal detected from a stimulation pulse to deliver effective therapy to the patient. The ECAP signal thus is representative of the distance between the stimulation electrodes and the nerves appropriate for the stimulation parameter values of the stimulation pulses delivered at that time. Therefore, processing circuitry 80 may attempt to use detected changes to the measured ECAP characteristic value to change stimulation pulse parameter values and maintain the target ECAP characteristic value during delivery of the primary stimulation pulses and master stimulation pulse.

Therefore, IMD 14 may be configured to provide ECAP responsive stimulation therapy to patient 12. Stimulation adjustments in response to changes in ECAP signals or to patient state may be automatic or semi-automatic (subject to patient approval). In many cases, fully automatic adjustments may be desirable so that IMD 14 may react more quickly to changes in patient state, or changes in therapy efficacy that may be unrelated to a change in patient state. In some examples, ECAP sensing and analysis may be used to refine stimulation therapy programs selected based on sensed posture.

Memory 82 may include definitions for each posture state of patient 12. In one example, the definitions of each posture state may be illustrated as a cone in three-dimensional space. Whenever the posture state parameter value, e.g., a vector, from the three-axis accelerometer of posture state module 86 resides within a predefined cone or volume, processing circuitry 80 indicates that patient 12 is in the posture state of the cone or volume. In other examples, a posture state parameter value from the 3-axis accelerometer may be compared to values in a look-up table or equation to determine the posture state in which patient 12 currently resides. Examples techniques for detecting a patient posture state include examples described in U.S. Pat. No. 8,708,934, titled "REORIENTATION OF PATIENT POSTURE STATES FOR POSTURE-RESPONSIVE THERAPY," filed Apr. 30, 2009 and issued Apr. 29, 2014, the entire content of which is incorporated by reference herein.

Although posture state module 86 is described as containing a 3-axis accelerometer, posture state module 86 may contain multiple single-axis accelerometers, dual-axis accelerometers, 3-axis accelerometers, or some combination thereof. In some examples, an accelerometer or other sensor may be located within or on IMD 14, on one of leads 16 (e.g., at the distal tip or at an intermediate position), an additional sensor lead positioned somewhere within patient 12, within an independent implantable sensor, or even worn on patient 12. For example, one or more microsensors may be implanted within patient 12 to communicate posture state information wirelessly to IMD 14. In this manner, the patient 12 posture state may be determined from multiple activity sensors placed at various locations on or within the body of patient 12.

In some examples, posture state module 86 may additionally or alternatively be configured to sense one or more physiological parameters of patient 12. For example, physiological parameters may include heart rate, electromyography (EMG), an electroencephalogram (EEG), an electrocardiogram (ECG), temperature, respiration rate, or pH. These physiological parameters may be used by processing circuitry 80, in some embodiments, to confirm or reject changes in sensed posture state that may result from vibration, patient travel (e.g., in an aircraft, car or train), or some other false positive of posture state. In some examples, the one or more physiological parameters may be used to determine a patient state other than posture. In addition, ECAP sensing and analysis may be used to confirm a change in the relationship between the stimulation source and stimulation target within patient 12.

Adjustments to one or more stimulation parameters responsive to changes in sensed ECAP may allow IMD 14 to implement a certain level of automation in therapy adjustments. In particular, IMD 14 may continuously, or on a periodic basis, adjust stimulation therapy parameters in order to maintain a target ECAP characteristic value that corresponds to efficacious treatment. Automatically adjusting stimulation may free patient 12 from the constant task of manually adjusting therapy each time patient 12 changes posture. Automatically adjusting stimulation based on sensed ECAP signal may also correct for natural drift of leads 16 irrespective of posture state. For example, by detecting ECAP signals over time, processing circuitry 80 may determine that the location of the nerves being stimulated has changed over time and automatically adjust therapy according to changing conditions without the need to receive changes for different patient states from patient 12 via programmer 20.

In addition, IMD 14 may store patient 12 input regarding perceived physiological conditions (e.g., symptoms) not detectable by any implemented sensors. For example, patient 12 may provide input to programmer 20 that indicates where the patient perceives any symptoms and characteristics of that particular type of symptom. processing circuitry 80 may associate this physiological condition information with the currently detected posture state, the stimulation parameters, and/or a time stamp to provide a complete therapy picture to the patient or clinician at a later time. Such information may be stored in memory 82 of IMD 14, the memory of programmer 20, and/or the memory of some other device.

Wireless telemetry in IMD 14 with external programmer 20, e.g., a patient programmer or a clinician programmer, or another device may be accomplished by radio frequency (RF) communication or proximal inductive interaction of IMD 14 with external programmer 20. Telemetry circuit 88 may send information to and receive information from external programmer 20 on a continuous basis, at periodic intervals, at non-periodic intervals, or upon request from the stimulator or programmer. To support RF communication, telemetry circuit 88 may include appropriate electronic components, such as amplifiers, filters, mixers, encoders, decoders, and the like.

Power source 90 delivers operating power to the components of IMD 14. Power source 90 may include a small rechargeable or non-rechargeable battery and a power generation circuit to produce the operating power. Recharging may be accomplished through proximal inductive interaction between an external charger and an inductive charging coil within IMD 14. In some embodiments, power requirements may be small enough to allow IMD 14 to utilize patient motion and implement a kinetic energy-scavenging device to trickle charge a rechargeable battery. In other embodiments, traditional batteries may be used for a limited period of time. As a further alternative, an external inductive power supply could transcutaneously power IMD 14 when needed or desired.

Sensing circuitry 92 may be configured to detects ECAP signals. In other examples, sensing circuitry 92 may be located on lead 16, and may include for, example, one or more of the electrodes in leads 16 in combination with suitable amplification, filtering and/or signal processing circuitry. In some examples, sensing circuitry 92 may include additional electrode on the housing of IMD 14. In some examples, Sensing circuitry 92 may be carried by an additional sensor lead positioned somewhere within patient 12, provided as an independent implantable sensor, or even worn on patient 12. For example, one or more microsensors may be implanted within patient 12 to communicate sensed ECAP signals, or characteristic values, wirelessly to IMD 14. In this manner the ECAP signals may be obtained independent of the location of the electrodes delivering electrical stimulation therapy.

In accordance with the techniques of the disclosure, IMD 14 may use ECAPs to adaptively adjust parameter values of high frequency electrical stimulation. In one example, processing circuitry 80 controls stimulation generator 84 to generate high frequency stimulation as trains of high frequency electrical stimulation pulses for delivery to patient 12 via leads 16, with a pause between each train where no high frequency electrical stimulation is delivered.

In some examples, each pulse of the train of pulses is defined by the same stimulation parameter values. In other examples, a train of electrical stimulation pulses comprises a plurality of primary electrical stimulation pulses followed by a master electrical stimulation pulse, where the master electrical stimulation pulse is different than the primary electrical stimulation pulses. For example, the primary electrical stimulation pulses may be configured to provide therapy to patient 12. The master electrical stimulation pulse may be configured to evoke an ECAP response from a tissue of patient 12 during the pause in high frequency electrical stimulation. The master electrical stimulation pulse may, or may not, provide some therapeutic effect to patient 12.

An exemplary range of electrical stimulation parameters are listed below. However, other parameter values are contemplated. While stimulation pulses are described, stimulation signals may be of any of a variety of forms such as sine waves or the like.

Each train of electrical stimulation pulses may be at least partially defined by a number of pulses, a pulse frequency and a burst frequency. The pulse frequency defines a frequency at which each pulse within a train is delivered to the patient. The burst frequency defines a frequency at which each train of one or more pulses is delivered to the patient. Typically, the pulse frequency is higher than the burst frequency. In some examples, each train of electrical stimulation pulses comprises a pulse frequency is selected from a range greater than or equal to 500 Hertz and less than or equal to 20 kilohertz. In some examples, each train of electrical stimulation pulses comprises a pulse frequency of about 1.2 kilohertz. In some examples, a burst frequency defining the frequency of the trains of pulses is selected from a range of about 1 Hertz to about 200 Hertz. In some examples, the pause between each train is greater than or equal to 1 millisecond.

In some examples, each pulse of a train comprises a pulse amplitude selected from a range of about 1 milliamp to about 25 milliamps. In some examples, each pulse of a train comprises a pulse width selected from a range of about 30 microseconds to about 300 microseconds. In some examples, each primary pulse of a train comprises a pulse width selected from a range of about 90 microseconds. In some examples, each master pulse of a train comprises a pulse width selected from a range of between about 60 microseconds to about 0.5 milliseconds.

Typically, the number of pulses in a train is a function of the pulse frequency. For example, for a pulse train comprising a high pulse frequency, the pulse train may comprise hundreds of pulses or more. As another example, for a pulse train comprising a low pulse frequency, the pulse train may comprise only a couple of pulses. In some examples, each train of pulses may include 2 or more, 5 or more, or 10 or more pulses. In another example, the train of electrical stimulation comprises 10 electrical stimulation pulses (e.g., 9 primary electrical stimulation pulses and 1 master electrical stimulation pulse).

Typically, the master electrical stimulation pulse comprises one or more parameter values that are different from the parameter values defining the primary electrical stimulation pulses. For example, the master electrical stimulation pulse comprises one or more of a current amplitude or a pulse width that is greater than the primary electrical stimulation pulses. In some examples, each of the primary electrical stimulation pulses comprises a current amplitude of about 0.4 milliamps and the master electrical stimulation pulse comprises a current amplitude of about 1.0 milliamps.

In some examples, when adjusting one or more parameters of the electrical stimulation therapy, processing circuitry 80 maintains a ratio of the value one or more parameters of the primary electrical stimulation pulses to the value of one or more parameters of the master electrical stimulation pulse. As an example, processing circuitry 80 controls stimulation generator 84 to generate a pulse train of a plurality of primary electrical stimulation pulses followed by a master electrical stimulation pulse. Each of the primary electrical stimulation pulses comprises a current amplitude of about 0.4 milliamps and the master electrical stimulation pulse comprises a current amplitude of about 1.0 milliamps (e.g., ratio of an amplitude of the primary electrical stimulation pulses to the master electrical stimulation pulse is 0.4 milliamps to 1.0 milliamps, or 1:2.5). Processing circuitry 80 may adjust, in response to a sensed ECAP signal, a current amplitude of the pulse train according to an incremental step size while maintaining the ratio of the primary electrical stimulation pulses to the master electrical stimulation pulse.

For example, when increasing an amplitude of the pulse train by a 10% step increment, processing circuitry 80 controls stimulation generator 84 to increase a current amplitude of the primary electrical stimulation pulses from 0.4 milliamps to about 0.44 milliamps and a current amplitude of the master electrical stimulation pulse from 1.0 milliamps to about 1.1 milliamps (e.g., a ratio of 1:2.5). As another example, when decreasing an amplitude of the pulse train by a 10% step decrement, processing circuitry 80 controls stimulation generator 84 to decrease a current amplitude of the primary electrical stimulation pulses from 0.4 milliamps to about 0.36 milliamps and a current amplitude of the master electrical stimulation pulse from 1.0 milliamps to about 0.9 milliamps (e.g., a ratio of 1:2.5).

By temporarily pausing the high frequency stimulation for a predetermined amount of time, sensing circuitry 92 may sense an ECAP signal from a target nerve of patient 12 during this amount of time without interference from the high frequency stimulation. Therefore, processing circuitry 80 may use the sensed ECAP to adjust values of one or more parameters of the high frequency electrical stimulation pulse train. In some examples, processing circuitry 80 controls stimulation generator 84 to modify one or more parameters of the last electrical stimulation pulse of the train to elicit a detectable ECAP.

Additionally or alternatively, processing circuitry 80 may control stimulation generator 84 to deliver low frequency electrical stimulation during the pause in the high frequency electrical stimulation pulse train so as to elicit the ECAP response and/or maintain therapeutic efficacy in patient 12 during the pause. For example, the low frequency electrical stimulation may comprise a plurality of electrical stimulation pulses delivered with a pulse frequency less than 500 Hertz. In some examples, the low frequency electrical stimulation comprises a plurality of electrical stimulation pulses delivered at about 50 Hertz. In this fashion, patient 12 may not experience an interruption, or less of an interruption, in therapy during the pause while high frequency stimulation is paused and sensing circuitry 92 senses an ECAP from a tissue of patient 12.

In some examples, processing circuitry 80 may use a posture of patient 86 sensed via posture state module 86 to adjust a rate at which ECAPs of patient 12 are sensed. For example, processing circuitry 80 may control stimulation generator 84 to deliver first trains of high frequency electrical stimulation pulses to patient 12. Each of the first trains of electrical stimulation pulses comprise a plurality of primary pulses configured to provide therapy to patient 12. In some examples, processing circuitry 80 may not include a pause in delivery of electrical stimulation between the first trains of high frequency electrical stimulation pulses. Periodically, and on a time-interleaved basis, processing circuitry 80 may control stimulation generator 84 to deliver a second train of high frequency electrical stimulation pulses to patient 12 followed by a pause in delivery of high frequency electrical stimulation therapy. The second train of electrical stimulation pulses comprises a plurality of primary pulses configured to provide therapy to patient 12 followed by a master pulse configured to evoke an ECAP signal of the patient. Processing circuitry 80 may control the rate of ECAP sensing of patient 12 by controlling the rate at which the second trains of high frequency electrical stimulation therapy are delivered to patient 12. For example, in response to a change in posture of patient 12, processing circuitry 80 may adjust the rate at which the second trains of high frequency electrical stimulation therapy are delivered to patient 12.

As another example, processing circuitry 80 may deliver only the first trains of high frequency electrical stimulation therapy to patient 12 while the posture of patient 12 is constant. In response to detecting a change in posture of patient 12, processing circuitry 80 controls stimulation generator 84 to deliver the second train of high frequency electrical stimulation therapy followed by a pause in delivery of high frequency electrical stimulation therapy so as to evoke an ECAP signal that processing circuitry 80 can used as feedback to adjust a value of one or more parameters of the electrical stimulation therapy to account for the new posture of patient 12. In this fashion, processing circuitry 80 may deliver continuous electrical stimulation comprising the first trains of high frequency electrical stimulation therapy to patient 12 while the posture of patient 12 is constant, and in response to detecting a change in posture, use the second trains of high frequency electrical stimulation therapy to elicit an ECAP response to adjust one or more parameters of the high frequency electrical stimulation therapy to accommodate the new assumed posture of patient 12.

Accordingly, using the techniques described herein, processing circuitry 80 may pause delivery of high frequency electrical stimulation so as to allow time for stimulation generator 84 to evoke an ECAP and sensing circuitry 92 to sense the ECAP signal. The ECAP may otherwise not be detectable by systems that deliver, e.g., continuous high frequency electrical stimulation. Therefore, a medical device as described herein may avoid masking an ECAP signal of the patient with high frequency electrical stimulation, thereby allowing for the use of characteristic values of sensed ECAPs as control signals for titrating one or more parameters of the high frequency electrical stimulation therapy.

Figure 3:
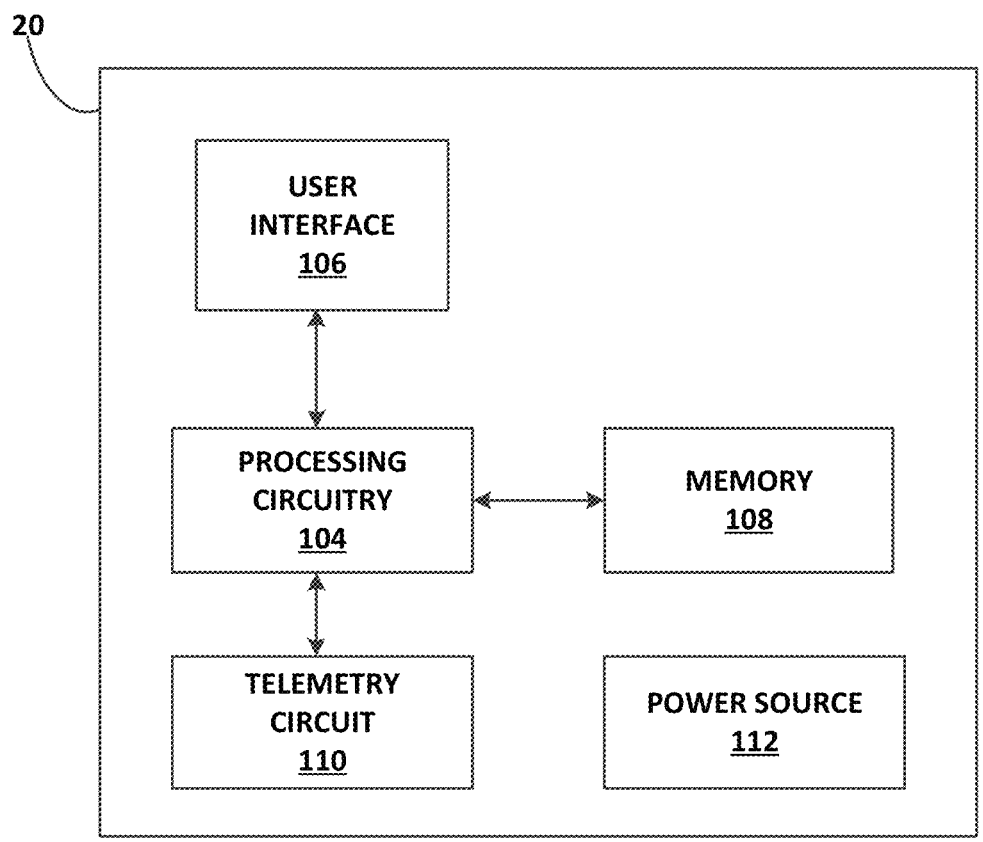
FIG. 3 is a functional block diagram illustrating example components of an external programmer for an IMD, such as the external programmer and IMD shown in FIG. 1.

FIG. 3 is a functional block diagram illustrating various components of an external programmer 20 for IMD 14. As shown in FIG. 3, external programmer 20 is an external device that includes processing circuitry 104, memory 108, telemetry circuit 110, user interface 106, and power source 112. External programmer 20 may be embodied as a patient programmer or a clinician programmer. A clinician or patient 12 interacts with user interface 106 in order to manually change the stimulation parameters of a program, change programs within a group, turn ECAP responsive stimulation ON or OFF, view therapy information, view patient state information, view a posture state indication, or otherwise communicate with IMD 14.

User interface 106 may include a screen and one or more input buttons, as in the example of a programmer, that allow external programmer 20 to receive input from a user. Alternatively, user interface 106 may additionally or only utilize a touch screen display, as in the example of a clinician programmer. The screen may be a liquid crystal display (LCD), dot matrix display, organic light-emitting diode (OLED) display, touch screen, or any other device capable of delivering and/or accepting information. For visible posture state indications, a display screen may suffice. For audible and/or tactile posture state indications, programmer 20 may further include one or more audio speakers, voice synthesizer chips, piezoelectric buzzers, or the like. Input buttons for user interface 106 may include a touch pad, increase and decrease buttons, emergency shut off button, and other buttons to control the stimulation therapy, as described above with regard to programmer 20. Processing circuitry 104 controls user interface 106, retrieves data from memory 108 and stores data within memory 108. Processing circuitry 104 also controls the transmission of data through telemetry circuit 110 to IMDs 14 or 26. Memory 108 includes operation instructions for processing circuitry 104 and data related to patient 12 therapy.

Telemetry circuit 110 allows the transfer of data to and from IMD 14. Telemetry circuit 110 may communicate automatically with IMD 14 in real-time, at a scheduled time, or when the telemetry circuit detects the proximity of the stimulator. User interface 106 may then update displayed information accordingly. Alternatively, telemetry circuit 110 may communicate with IMD 14 when signaled by a user through user interface 106. To support RF communication, telemetry circuit 110 may include appropriate electronic components, such as amplifiers, filters, mixers, encoders, decoders, and the like. Power source 112 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter.

In some examples, external programmer 20 may be configured to recharge IMD 14 in addition to programming IMD 14. Alternatively, a recharging device may be capable of communication with IMD 14. Then, the recharging device may be able to transfer programming information, data, or any other information described herein to IMD 14. In this manner, the recharging device may be able to act as an intermediary communication device between external programmer 20 and IMD 14. In other cases, the programmer may be integrated with a recharging functionality in the combined programming/recharging device. The techniques described herein may be communicated between IMD 14 via any type of external device capable of communication with IMD 14.

Figure 4A:
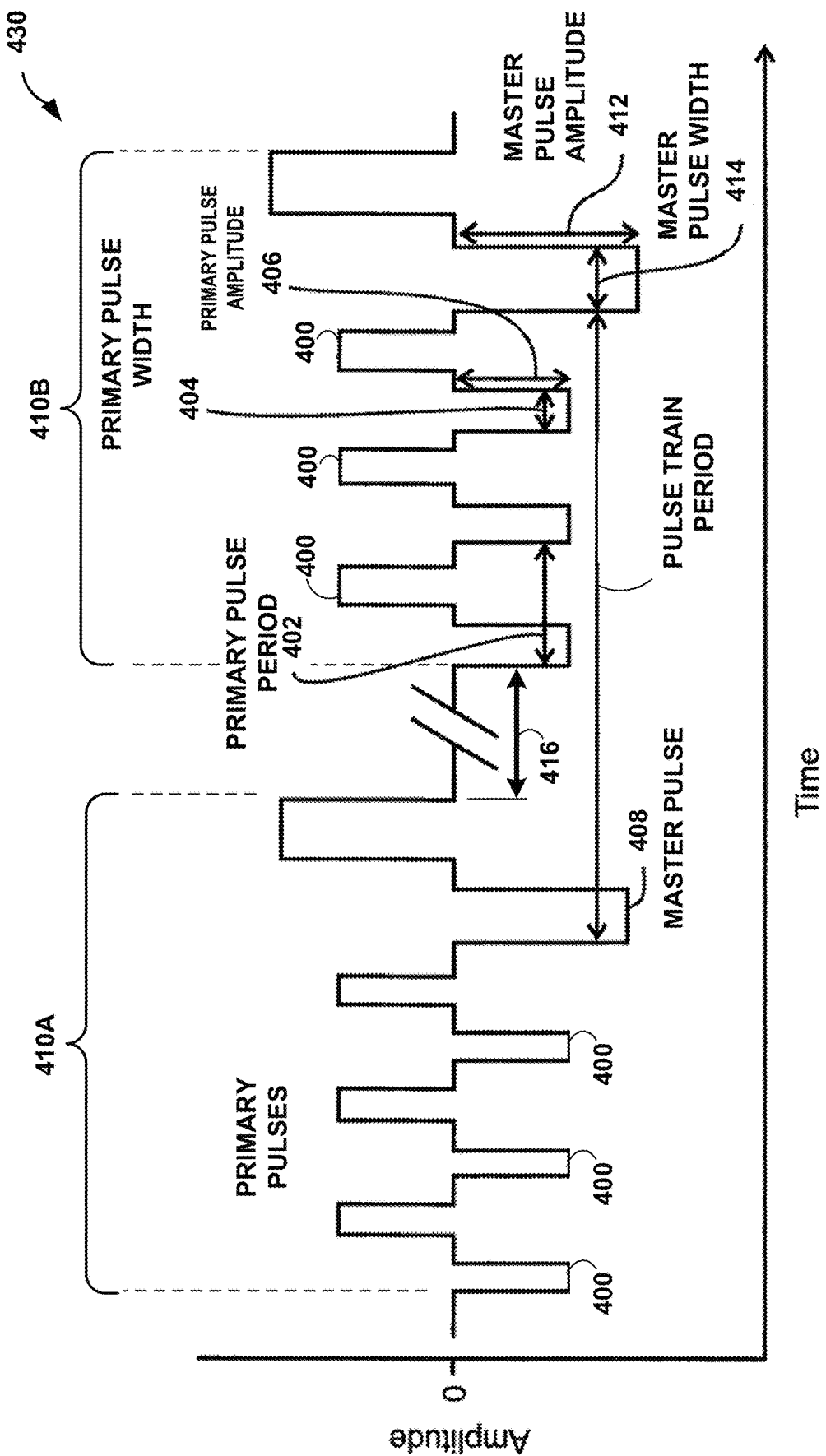
FIGS. 4A, 4B, and 4C are graphs illustrating example trains of electrical stimulation pulses in accordance with the techniques of the disclosure.
Figure 4B:
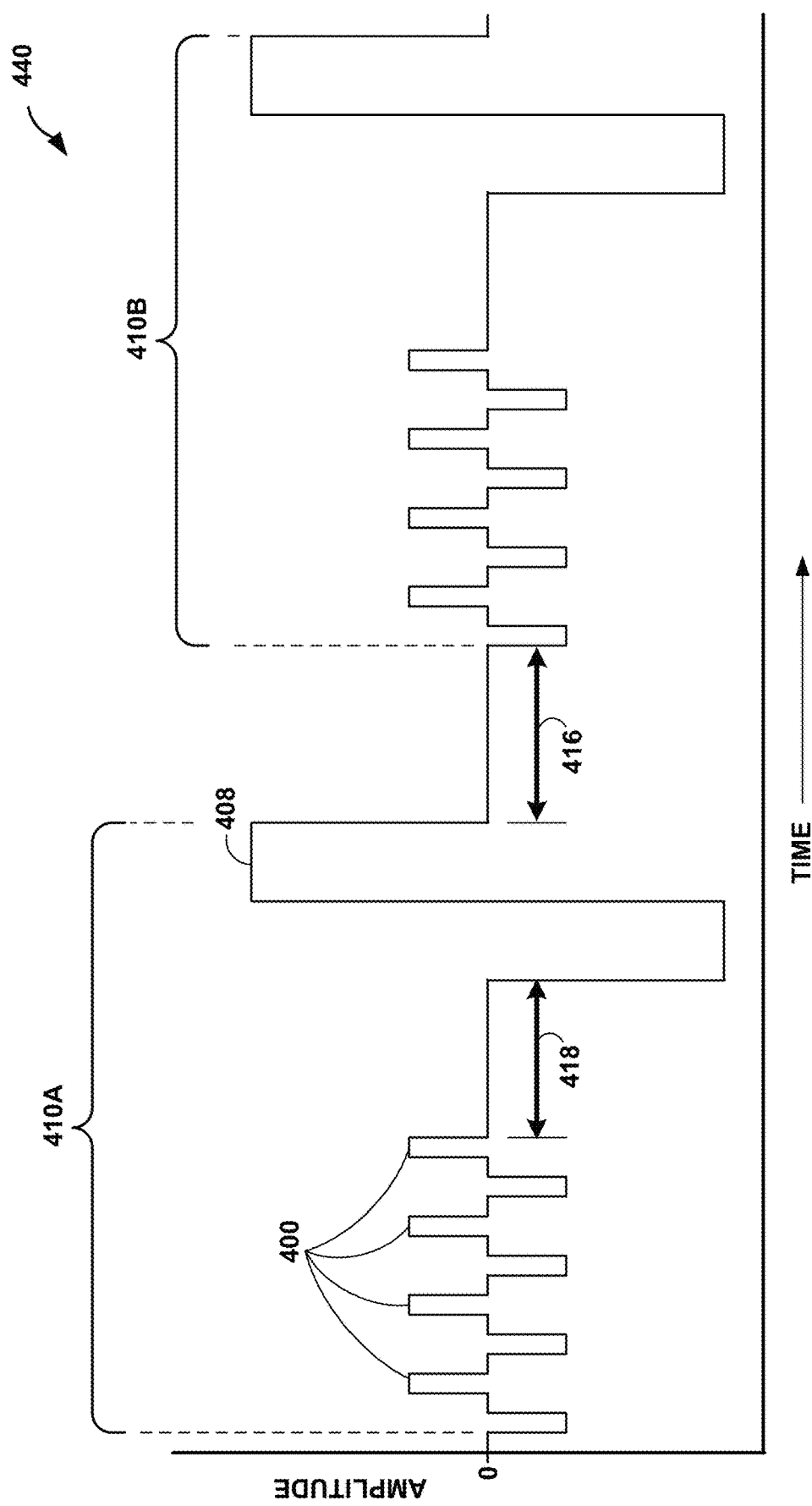
Figure 4C:
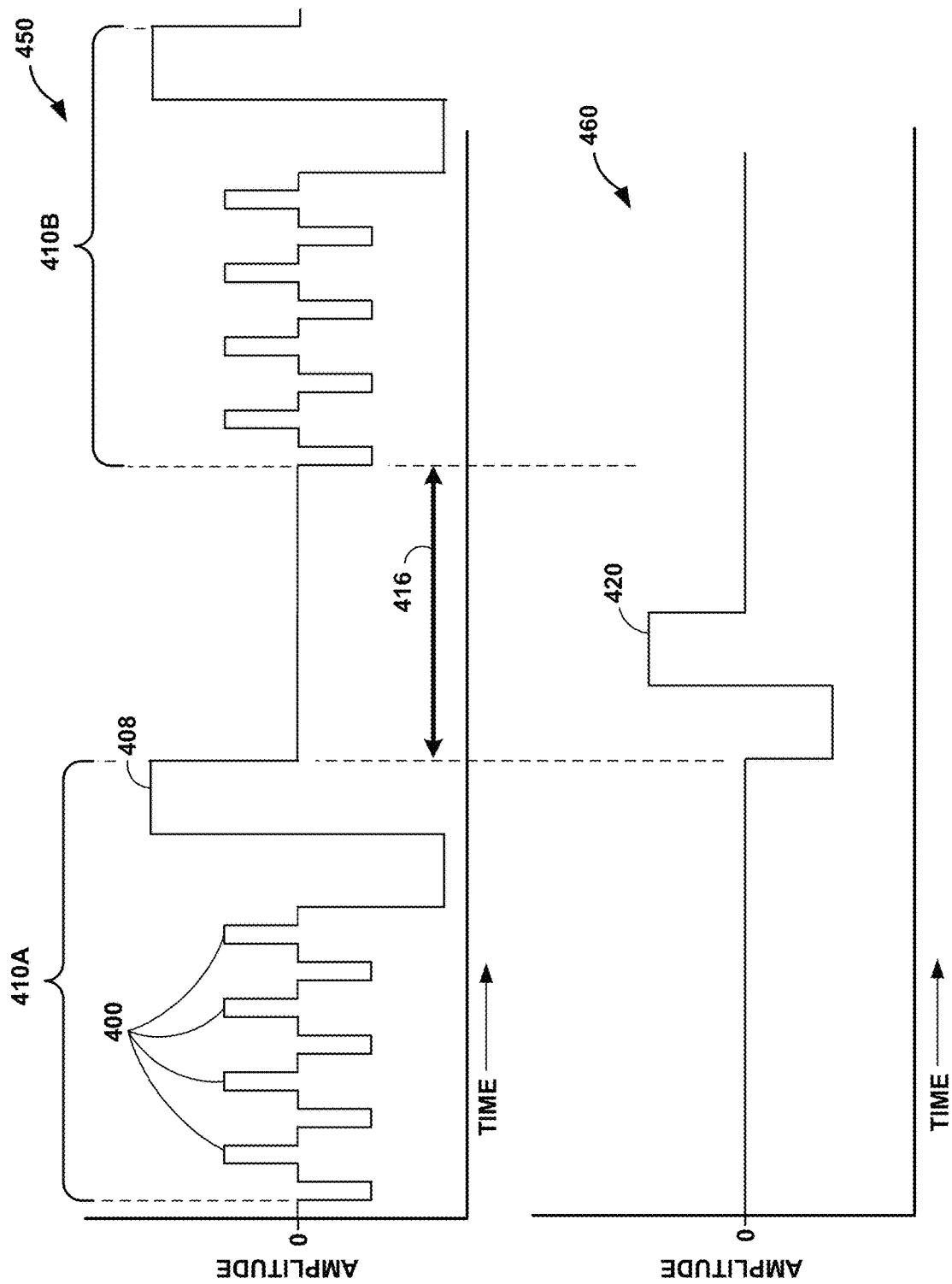

FIGS. 4A, 4B, and 4C are graphs illustrating example trains of electrical stimulation pulses in accordance with the techniques of the disclosure. For convenience, FIGS. 4A-4C are described with respect to IMD 14 of FIGS. 1 and 2.

FIG. 4A illustrates an example stimulation signal 430 of high frequency electrical stimulation pulses comprising first pulse train 410A and second pulse train 410B. Each of pulse trains 410A, 410B (collectively, "trains 410") comprise a plurality of primary electrical stimulation pulses 400 followed by a master electrical stimulation pulse 408. Stimulation signal 430 may be generated, e.g., by stimulation generator 84 of IMD 14 of FIG. 2.

Primary electrical stimulation pulses 400 may be configured to provide therapy to patient 12. In contrast, master electrical stimulation pulse 408 may be configured to evoke an ECAP response from a tissue of patient 12 which may be sensed by IMD 14 during pause 416 between two successive trains 410A, 410B of high frequency electrical stimulation pulses. IMD 14 may use the ECAP resulting from master electrical stimulation pulse 408 to adapt one or more parameters of either or both of primary electrical stimulation pulses 400 and master electrical stimulation pulse 408 (e.g., an amplitude or pulse width of pulses 400, 408). In some examples, IMD 14 adjusts both of primary electrical stimulation pulses 400 and master electrical stimulation pulse 408 in a ratiometric fashion (e.g., to preserve a ratio of one or more parameters of primary electrical stimulation pulses 400 to one or more parameters of master electrical stimulation pulse 408).

Master electrical stimulation pulse 408 is defined by different parameter values than primary electrical stimulation pulses 400. As depicted in FIG. 4A, master electrical stimulation pulse 408 has a greater pulse width 414 and a greater pulse amplitude 412 as compared to a pulse width 404 and a pulse amplitude 406 primary electrical stimulation pulses 400. Although pulses 400, 408 forming train 410A are depicted with a square morphology, the morphology of the pulse may be a triangle, sinusoid, gaussian, exponential, ramp, or any morphology or combination thereof that serves to deliver charge to and from a target tissue of patient 12.

In some examples, the number of primary electrical stimulation pulses 400 is selected from a range greater than or equal to 2 and less than or equal to 50. In some examples, the number of primary electrical stimulation pulses 400 is 9, followed by a single master electrical stimulation pulse 408.

A primary pulse interval 402 and a pulse width 404 of primary electrical stimulation pulses 400 may be fixed or variable. Each of primary electrical stimulation pulses 400 may have asymmetrical primary pulse widths 402 for anodic and cathodic phases.

Stimulation signal 430 further includes an inter-pulse interval 416 (also referred to herein as a "pause") during which no charge is delivered to patient 12. Sensing circuitry 92 of IMD 14 may sense, during pause interval 416, an ECAP response of patient 12 evoked by master electrical stimulation pulse 408. The use of pause interval 416 may reduce the instance of primary electrical stimulation pulses 400 masking and/or causing interference to the ECAP response of patient 12 such that IMD 14 may use one or more characteristic values of the ECAP response to adjust one or more parameters of either or both of primary electrical stimulation pulses 400 or master electrical stimulation pulse 408.

FIG. 4B illustrates an example stimulation signal 440 of high frequency electrical stimulation pulses comprising first pulse train 410A and second pulse train 410B. Each of pulse trains 410A, 410B comprise a plurality of primary electrical stimulation pulses 400 followed by a master electrical stimulation pulse 408. Trains 440 may be generated, e.g., by stimulation generator 84 of IMD 14 of FIG. 2. Stimulation signal 440 may be substantially similar to stimulation signal 430 of FIG. 4A. However, stimulation signal 440 further includes an inter-pulse interval 418 during which no charge is delivered to patient 12. Inter-pulse interval 418 is interposed between the last primary electrical stimulation pulse 400 and master electrical stimulation pulse 408.

As described above with respect to FIG. 4A, sensing circuitry 92 of IMD 14 senses, during pause interval 416, a first ECAP signal of patient 12 evoked by master electrical stimulation pulse 408. Furthermore, sensing circuitry 92 of IMD 14 senses, during pause interval 418, a second ECAP signal of patient 12 evoked by the last primary electrical stimulation pulse 400. The use of pause intervals 416 and 418 may reduce the instance of primary electrical stimulation pulses 400 masking and/or causing interference to the ECAP signal of patient 12 such that IMD 14 may use one or more characteristic values of the first and second ECAP signals to control adjustment of one or more parameters of either or both of primary electrical stimulation pulses 400 or master electrical stimulation pulse 408.

Furthermore, the first ECAP signal to the last primary electrical stimulation pulse 400 may exhibit different morphology than the second ECAP response to master electrical stimulation pulse 408. IMD 14, or a clinician reviewing the first and second ECAP signals, may use a morphological difference between the first and second ECAP signals to further adjust a value of one or more parameters that define either or both of primary electrical stimulation pulses 400 or master electrical stimulation pulse 408.

FIG. 4C illustrates example high frequency stimulation signal 450 and low frequency stimulation signal 460. High frequency stimulation signal 450 comprises high frequency first pulse train 410A and second pulse train 410B. Each of trains 410 comprise a plurality of primary electrical stimulation pulses 400 followed by a master electrical stimulation pulse 408. Low frequency stimulation signal 460 comprises a low frequency pulse train 420 of one or more low frequency electrical stimulation pulses. Stimulation signals 450 and 460 may be generated, e.g., by stimulation generator 84 of IMD 14 of FIG. 2. Stimulation signal 450 may be substantially similar to stimulation signal 430 of FIG. 4A.

As depicted in the example of FIG. 4C, during interval 416, IMD delivers train 420 of low frequency electrical stimulation pulses to patient 12. After pause 416 elapses, IMD 14 may cease delivery of train 420 of low frequency electrical stimulation pulses and resume delivery of train 410B of high frequency electrical stimulation pulses. In some examples, electrical stimulation pulses 420 comprise a pulse frequency less than 500 Hertz. In some examples, electrical stimulation pulses 420 comprise a pulse frequency of about 50 Hertz.

Train 420 of low frequency electrical stimulation pulses may not substantially mask or interfere with the sensing of ECAP signals sensed from patient 12. For example, electrical stimulation pulses 420 may be configured to elicit the ECAP response from patient 12. Additionally or alternatively, electrical stimulation pulses 420 may be configured to maintain therapeutic efficacy in patient 12 during the pause 416 between trains 410A and 410B of high frequency electrical stimulation pulses. Thus, by delivering train 420 of low frequency electrical stimulation pulses during the pause 416 between trains 410A and 410B of high frequency electrical stimulation pulses, IMD 14 may avoid causing an interruption in therapy to patient 12 during pause 416 while sensing the ECAP from the tissue of patient 12.

Figure 5:
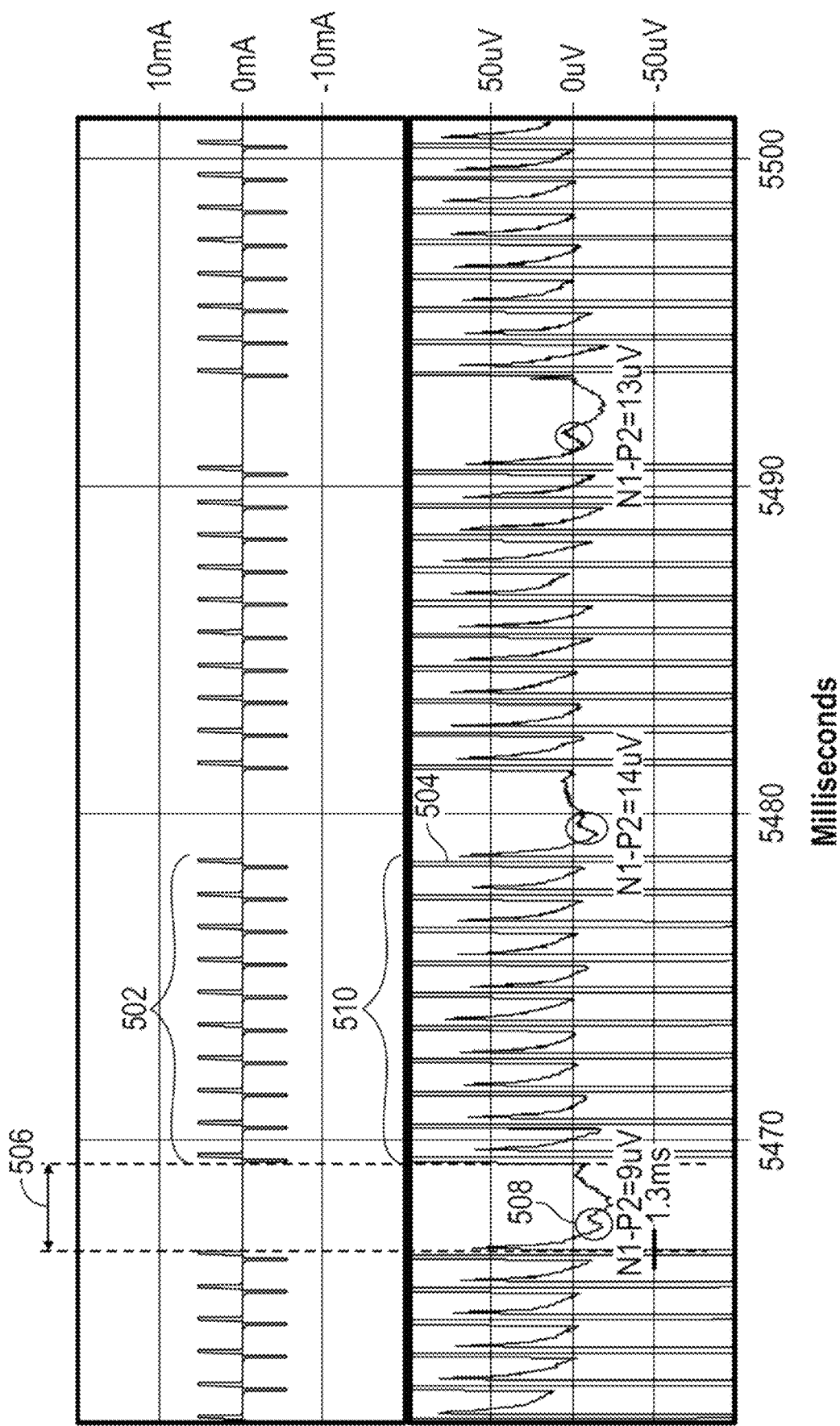
FIG. 5 is a graph illustrating example trains of electrical stimulation pulses and a signal sensed from a patient response in accordance with the techniques of the disclosure.

FIG. 5 is a graph illustrating example stimulation trains 502 of electrical stimulation pulses and an ECAP signal 504 sensed from a patient in accordance with the techniques of the disclosure. For convenience, FIG. 5 is described with respect to IMD 14 of FIGS. 1 and 2.

High frequency stimulation may employ other mechanisms of action besides a sensation of paresthesia as compared with low frequency stimulation. However, high frequency stimulation effects can change if electrode location changes with respect to a target nerve. As such, the incorporation of a feedback control system into a high frequency SCS system to can provide more consistent, even therapy to a patient. However, high frequency electrical stimulation pulses may mask an ECAP response of the patient. For example, resolving an ECAP signal in the presence of high frequency stimulation is particularly challenging because high frequency stimulation may induce greater stimulation artifact as compared with low frequency stimulation. Stimulation artifact is a non-linear aggressor which manifests concurrently with the delivery of the high frequency electrical stimulation pulse. Stimulation artifact serves to confound the ability of a medical device system, such as IMD 14, to resolve an ECAP signal of a tissue of patient 12. Therefore, a high frequency SCS system may be unable to resolve an ECAP signal in the presence of high frequency stimulation.

In accordance with the techniques of the disclosure, a medical device system temporarily pauses delivery of high frequency electrical stimulation pulses. The pause in high frequency electrical stimulation allows a brief window for the ECAP signal to manifest and be detected before the next high frequency electrical stimulation pulse is delivered. In some examples, high frequency stimulation is a train of two or more stimulation pulses comprising a pulse frequency greater than or equal to 500 Hertz. The train may be repeated at a burst frequency of 1 Hertz to 200 Hertz, wherein IMD 14 interposes at least a 1 millisecond pause between the end of a first stimulation train and the beginning of a second stimulation train. Accordingly, using the techniques disclosed herein, IMD 14 may use ECAPs to titrate high frequency stimulation without masking the ECAPS with the high frequency electrical stimulation pulses.

As depicted in FIG. 5, processing circuitry 80 controls stimulation generator 84 to generate train 502 of electrical stimulation pulses for delivery to patient 12. In the example of FIG. 5, stimulation generator 84 generates train 502 of 10 balanced, biphasic pulses comprising a pulse frequency of 1,000 Hertz, a pulse amplitude of 5.75 milliamps, and a pulse width of 90 microseconds. Processing circuitry 80 controls stimulation generator 84 to deliver each train 502 every 12 milliseconds (e.g., a burst rate of 83.3 Hertz). Processing circuitry 80 controls stimulation generator 84 to cease delivery of high frequency electrical stimulation for a pause interval 506 of 2 milliseconds.

During pause interval 506, Sensing circuitry 92 senses a signal from patient 12 indicative of an ECAP response to train 502. As illustrated in FIG. 5, during delivery of electrical stimulation train 502, the electrical stimulation delivered by stimulation generator 84 induces noise 510. Noise 510 is of a much greater magnitude than an ECAP response of patient 12 and may render Sensing circuitry 92 unable to detect the ECAP response of patient 12. Through the use of pause interval 506, Sensing circuitry 92 is able to sense a clean, artifact-free ECAP response 508 of patient 12. Pause interval 506 is selected so as to allow sufficient time for ECAP response 508 to manifest, as ECAP response 508 may otherwise be undetectable in the presence of high frequency electrical stimulation. Thereafter, processing circuitry 80 may use ECAP response 508 to adjust one or more parameters of the delivered high frequency electrical stimulation as described above.

Figure 6:
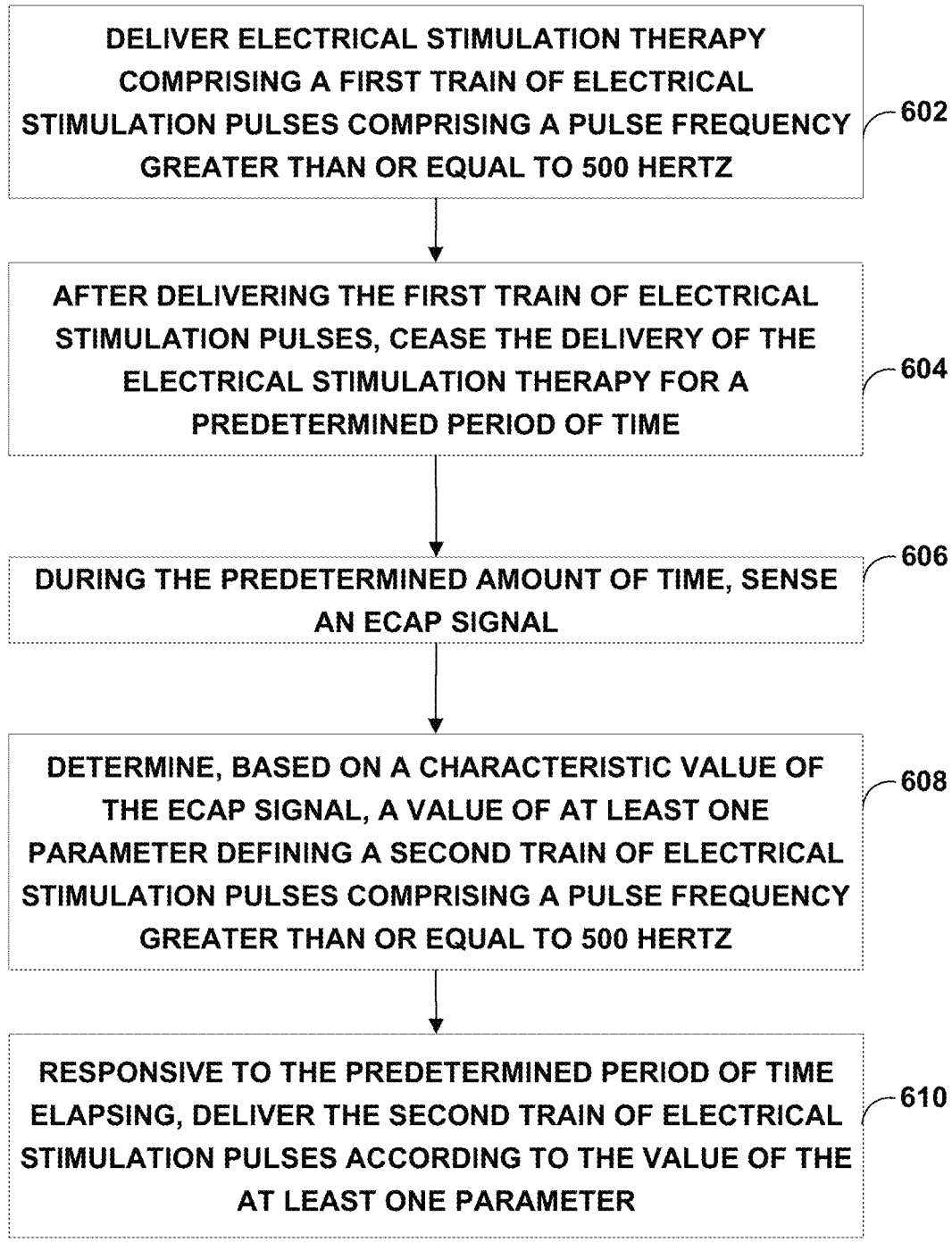
FIG. 6 is a flowchart illustrating an operation in accordance with the techniques of the disclosure.

FIG. 6 is a flowchart illustrating an operation in accordance with the techniques of the disclosure. Specifically, the flowchart of FIG. 6 depicts an operation for using an ECAP response of a patient to adjust one or more parameters of electrical stimulation therapy comprising a train of high frequency electrical stimulation pulses. For convenience, FIG. 6 is described with respect to IMD 14 and processing circuitry 80 of FIGS. 1 and 2.

As depicted in the example of FIG. 6, processing circuitry 80 controls stimulation generator 84 to deliver electrical stimulation therapy comprising a first train of electrical stimulation therapy pulses to patient 12 (602). In some examples, the first train of electrical stimulation therapy pulses comprises a pulse frequency greater than or equal to 500 Hertz. In some examples, the train of electrical stimulation pulses comprises a plurality of primary electrical stimulation pulses followed by a master electrical stimulation pulse. The primary electrical stimulation pulses may be configured to provide therapy to patient 12. The master electrical stimulation pulse may be configured to evoke an ECAP response from a tissue of patient 12 during the pause in high frequency electrical stimulation. However, in some examples, the master electrical stimulation pulse may provide some therapeutic benefit to patient 12.

After delivering the first train of electrical stimulation pulses, processing circuitry 80 controls stimulation generator 84 to cease the delivery of the electrical stimulation therapy for a predetermined period of time (604). In some examples, the predetermined period of time is greater than or equal to 1 millisecond.

During the predetermined period of time, sensing circuitry 92 senses an ECAP signal from a tissue of patient 12 (606). Additionally or alternatively, processing circuitry 80 may control stimulation generator 84 to deliver low frequency electrical stimulation during the predetermined period of time so as to elicit the ECAP response and/or maintain therapeutic efficacy in patient 12 while the high frequency electrical stimulation therapy is halted. For example, the low frequency electrical stimulation may comprise a plurality of electrical stimulation pulses delivered a pulse frequency of less than 500 Hertz. In some examples, the low frequency electrical stimulation comprises a plurality of electrical stimulation pulses delivered at about 50 Hertz. In this fashion, patient 12 may not experience an interruption in therapy during the pause while sensing circuitry 92 senses an ECAP from a tissue of patient 12. Processing circuitry 80 may also determine a characteristic value of the sensed ECAP signal that processing circuitry 80 may compare to a target ECAP characteristic value.

Processing circuitry 80 determines, based on a characteristic value of the sensed ECAP signal, a value of at least one parameter at least partially defining a second train of electrical stimulation pulses (608). In some examples, the second train of electrical stimulation therapy pulses comprises a pulse frequency greater than or equal to 500 Hertz. For example, the sensed ECAP signal may be indicative of a distance of electrodes disposed along leads 16 to a target nerve of patient 12. Processing circuitry 80 compares a characteristic value of the ECAP signal to a target characteristic value for the ECAP. If the characteristic value of the ECAP signal is greater than the target characteristic value for the ECAP, the ECAP signal may be indicative that the electrodes disposed along leads 16 have shifted closer to the target nerve, and a commensurate reduction in one or more parameters (such as an amplitude) of the high frequency electrical stimulation pulses is necessary to maintain a constant level of therapy to patient 12.

Conversely, if the characteristic value of the ECAP signal is less than the target characteristic value for the ECAP, the ECAP signal may be indicative that the electrodes disposed along leads 16 have shifted away from the target nerve, and a commensurate increase in one or more parameters (such as an amplitude) of the high frequency electrical stimulation pulses is necessary to maintain a constant level of therapy to patient 12. Based on the comparison, processing circuitry 80 determines a value of the at least one parameter defining the second train of electrical stimulation therapy pulses so as to reduce the difference between the characteristic value of the ECAP signal and the target characteristic value for the ECAP.

Responsive to the predetermined period of time elapsing, processing circuitry 80 controls stimulation generator 84 to deliver the second train of electrical stimulation pulses according to the value of the at least one parameter (610). Therefore, a medical device as described herein may avoid masking an ECAP response of patient 12 with high frequency electrical stimulation, thereby allowing for the use of one or more characteristic values of sensed ECAPs to control titration of one or more parameters of the high frequency electrical stimulation therapy.

The following examples may illustrate one or more aspects of the disclosure.

Example 1

A method that includes delivering, by a medical device, electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, ceasing, by the medical device, the delivery of the electrical stimulation therapy for a predetermined period of time; during the predetermined period of time, sensing, by the medical device, an evoked compound action potential (ECAP) signal from a tissue of the patient; determining, by the medical device and based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, delivering the second train of electrical stimulation pulses according to the value of the at least one parameter at least partially defining the second set of pulses.

Example 2

The method of example 1, wherein the ECAP signal comprises a first ECAP signal, and wherein the method further comprises: after delivering the second train of electrical stimulation pulses, ceasing, by the medical device, the delivery of the electrical stimulation therapy for the predetermined period of time; during the predetermined period of time, sensing, by the medical device, a second ECAP signal from the tissue of the patient; determining, by the medical device and based on a characteristic value of the second ECAP signal, a value of at least one parameter at least partially defining a third train of electrical stimulation pulses, wherein the third train of electrical stimulation pulses comprises a pulse frequency greater than or equal to 500 Hertz; and responsive to the predetermined period of time elapsing, delivering the third train of electrical stimulation pulses according to the value of the at least one parameter at least partially defining the second set of pulses.

Example 3

The method of any of examples 1 through 2, wherein: the first train of electrical stimulation pulses comprises a plurality of primary electrical stimulation pulses followed by a master electrical stimulation pulse, the plurality of primary electrical stimulation pulses are defined by a primary set of parameters and configured to contribute to therapy of the patient, and the master electrical stimulation pulse is defined by a master set of parameters and configured to evoke the ECAP signal from the tissue of the patient, wherein a value of the master set of parameters is different than a value of the primary set of parameters.

Example 4

The method of example 3, wherein the master electrical stimulation pulse of the first train comprises a current amplitude greater than a pulse amplitude of the plurality of primary electrical stimulation pulses of the first train.

Example 5

The method of any of examples 3 through 4, wherein the plurality of primary electrical stimulation pulses of the first train is a first primary current amplitude, wherein the master electrical stimulation pulse of the first train comprises a first master current amplitude, wherein the plurality of primary electrical stimulation pulses of the second train comprises a second primary current amplitude, wherein the master electrical stimulation pulse of the second train comprises a second master current amplitude, and wherein determining the value of the at least one parameter defining the second train of electrical stimulation pulses comprises: determining a value of the second primary current amplitude that is different from a value of the first primary current amplitude; determining a value of the second master current amplitude that is different from a value of the first master current amplitude, wherein a ratio of the second primary current amplitude to the second master current amplitude is the same as a ratio of the first primary current amplitude to the first master current amplitude.

Example 6

The method of example 5, wherein the value of the second primary current amplitude is greater than the value of the first primary current amplitude, wherein the value of the second master current amplitude is greater than the value of the first master current amplitude, and wherein the ratio of the second primary current amplitude to the second master current amplitude is the same as the ratio of the first primary current amplitude to the first master current amplitude.

Example 7

The method of any of examples 5 through 6, wherein the value of the second primary current amplitude is less than the value of the first primary current amplitude, wherein the value of the second master current amplitude is less than the value of the first master current amplitude, and wherein the ratio of the second primary current amplitude to the second master current amplitude is the same as the ratio of the first primary current amplitude to the first master current amplitude.

Example 8

The method of any of examples 1 through 7, wherein the method further comprises: during the predetermined period of time, delivering, by the medical device, electrical stimulation therapy comprising a third train of electrical stimulation pulses to the patient, wherein the third train of electrical stimulation pulses comprises a third pulse frequency less than 500 Hertz; and responsive to the predetermined period of time elapsing, ceasing the delivery of the electrical stimulation therapy comprising the third train of electrical stimulation pulses.

Example 9

The method of any of examples 1 through 8, further that includes delivering electrical stimulation therapy comprising a plurality of primary electrical stimulation pulses to the patient; detecting, by the medical device, a change in posture of the patient, wherein: delivering the electrical stimulation therapy comprising the first train of electrical stimulation pulses to the patient comprises delivering, in response to the detected change in posture of the patient, the first train of electrical stimulation pulses comprising the plurality of primary electrical stimulation pulses followed by a master electrical stimulation pulse to the patient, the plurality of primary electrical stimulation pulses are configured to provide therapy to the patient, and the master electrical stimulation pulse is configured to evoke the ECAP signal from the tissue of the patient.

Example 10

The method of any of examples 1 through 9, wherein the electrical stimulation therapy comprises a burst frequency greater than or equal 1 Hertz and less than or equal to 200 Hertz, wherein the burst frequency comprises a frequency at which the first train of electrical stimulation pulses and the second train of electrical stimulation pulses are delivered to the patient.

Example 11

The method of any of examples 1 through 10, wherein the medical device is an implantable medical device.

Example 12

A medical device configured to: deliver electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, cease the delivery of the electrical stimulation therapy for a predetermined period of time; during the predetermined period of time, sense an evoked compound action potential (ECAP) signal from a tissue of the patient; determine, based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, deliver the second train of electrical stimulation pulses according to the value of the at least one parameter at least partially defining the second set of pulses.

Example 13

The medical device of example 12, wherein the ECAP signal comprises a first ECAP signal, and wherein the medical device is further configured to: after delivering the second train of electrical stimulation pulses, cease the delivery of the electrical stimulation therapy for the predetermined period of time; during the predetermined period of time, sense a second ECAP signal from the tissue of the patient; determine, based on a characteristic value of the second ECAP signal, a value of at least one parameter at least partially defining a third train of electrical stimulation pulses, wherein the third train of electrical stimulation pulses comprises a pulse frequency greater than or equal to 500 Hertz; and responsive to the predetermined period of time elapsing, deliver the third train of electrical stimulation pulses according to the value of the at least one parameter at least partially defining the second set of pulses.

Example 14

The medical device of example 12, wherein: the first train of electrical stimulation pulses comprises a plurality of primary electrical stimulation pulses followed by a master electrical stimulation pulse, the plurality of primary electrical stimulation pulses are defined by a primary set of parameters and configured to contribute to therapy of the patient, and the master electrical stimulation pulse is defined by a master set of parameters and configured to evoke the ECAP signal from the tissue of the patient, wherein a value of the master set of parameters is different than a value of the primary set of parameters.

Example 15

The medical device of example 14, wherein the master electrical stimulation pulse of the first train comprises a current amplitude greater than a pulse amplitude of the plurality of primary electrical stimulation pulses of the first train.

Example 16

The medical device of any of examples 14 through 15, wherein the plurality of primary electrical stimulation pulses of the first train is a first primary current amplitude, wherein the master electrical stimulation pulse of the first train comprises a first master current amplitude, wherein the plurality of primary electrical stimulation pulses of the second train comprises a second primary current amplitude, wherein the master electrical stimulation pulse of the second train comprises a second master current amplitude, and wherein to determine the value of the at least one parameter defining the second train of electrical stimulation pulses, the medical device is configured to: determine a value of the second primary current amplitude that is different from a value of the first primary current amplitude; and determine a value of the second master current amplitude that is different from a value of the first master current amplitude, wherein a ratio of the second primary current amplitude to the second master current amplitude is the same as a ratio of the first primary current amplitude to the first master current amplitude.

Example 17

The medical device of example 16, wherein the value of the second primary current amplitude is greater than the value of the first primary current amplitude, wherein the value of the second master current amplitude is greater than the value of the first master current amplitude, and wherein the ratio of the second primary current amplitude to the second master current amplitude is the same as the ratio of the first primary current amplitude to the first master current amplitude.

Example 18

The medical device of any of examples 16 through 17, wherein the value of the second primary current amplitude is less than the value of the first primary current amplitude, wherein the value of the second master current amplitude is less than the value of the first master current amplitude, and wherein the ratio of the second primary current amplitude to the second master current amplitude is the same as the ratio of the first primary current amplitude to the first master current amplitude.

Example 19

The medical device of any of examples 12 through 18, wherein the medical device is further configured to: during the predetermined period of time, deliver electrical stimulation therapy comprising a third train of electrical stimulation pulses to the patient, wherein the third train of electrical stimulation pulses comprises a third pulse frequency less than 500 Hertz; and responsive to the predetermined period of time elapsing, cease the delivery of the electrical stimulation therapy comprising the third train of electrical stimulation pulses.

Example 20

A non-transitory, computer-readable medium comprising instructions that, when executed, are configured to cause processing circuitry of an implantable medical device to: control a stimulation generator of the implantable medical device to deliver electrical stimulation therapy comprising a first train of electrical stimulation pulses to a patient, wherein the first train of electrical stimulation pulses comprises a first pulse frequency greater than or equal to 500 Hertz; after delivering the first train of electrical stimulation pulses, control the stimulation generator to cease the delivery of the electrical stimulation therapy for a predetermined period of time; during the predetermined period of time, sense an evoked compound action potential (ECAP) signal from a tissue of the patient; determine, based on a characteristic value of the ECAP signal, a value of at least one parameter at least partially defining a second train of electrical stimulation pulses, wherein the second train of electrical stimulation pulses comprises a second pulse frequency greater than or equal to 500 Hertz; and responsive to the predetermined period of time elapsing, control the stimulation generator to deliver the second train of electrical stimulation pulses according to the value of the at least one parameter at least partially defining the second set of pulses.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Various examples have been described. These and other examples are within the scope of the following claims.

What is claimed is:

1. A method comprising:
    delivering, by a medical device, electrical stimulation therapy comprising a first train of electrical stimulation pulses and a second train of electrical stimulation pulses to a patient, wherein the first train of electrical stimulation pulses comprises a first pulse frequency greater than or equal to 500 Hertz, and wherein the first train of electrical stimulation pulses is separated from the second train of electrical stimulation pulse by a predetermined period of time;
    after delivering the first train of electrical stimulation pulses, ceasing, by the medical device, the delivery of the electrical stimulation therapy for the predetermined period of time;
    during the predetermined period of time, sensing, by the medical device, an evoked compound action potential (ECAP) signal from a tissue of the patient;
    determining, by the medical device and based on a characteristic value of the ECAP signal, a value of at least one parameter at least partially defining the second train of electrical stimulation pulses, wherein the second train of electrical stimulation pulses comprises a second pulse frequency greater than or equal to 500 Hertz; and
    responsive to the predetermined period of time elapsing, delivering the second train of electrical stimulation pulses according to the value of the at least one parameter at least partially defining the second set of pulses.

2. The method of claim 1,
wherein the ECAP signal comprises a first ECAP signal, and
wherein the method further comprises:
    after delivering the second train of electrical stimulation pulses, ceasing, by the medical device, the delivery of the electrical stimulation therapy for the predetermined period of time;
    during the predetermined period of time, sensing, by the medical device, a second ECAP signal from the tissue of the patient;
    determining, by the medical device and based on a characteristic value of the second ECAP signal, a value of at least one parameter at least partially defining a third train of electrical stimulation pulses, wherein the third train of electrical stimulation pulses comprises a pulse frequency greater than or equal to 500 Hertz; and
    responsive to the predetermined period of time elapsing, delivering the third train of electrical stimulation pulses according to the value of the at least one parameter at least partially defining the second set of pulses.

3. The method of claim 1, wherein:
    the first train of electrical stimulation pulses comprises a plurality of primary electrical stimulation pulses followed by a master electrical stimulation pulse,
    the plurality of primary electrical stimulation pulses are defined by a primary set of parameters and configured to contribute to therapy of the patient, and
    the master electrical stimulation pulse is defined by a master set of parameters and configured to evoke the ECAP signal from the tissue of the patient, wherein a value of the master set of parameters is different than a value of the primary set of parameters.

4. The method of claim 3, wherein the master electrical stimulation pulse of the first train comprises a current amplitude greater than a pulse amplitude of the plurality of primary electrical stimulation pulses of the first train.

5. The method of claim 3,
wherein the plurality of primary electrical stimulation pulses of the first train is a first primary current amplitude,
wherein the master electrical stimulation pulse of the first train comprises a first master current amplitude,
wherein the plurality of primary electrical stimulation pulses of the second train comprises a second primary current amplitude,
wherein the master electrical stimulation pulse of the second train comprises a second master current amplitude, and
wherein determining the value of the at least one parameter defining the second train of electrical stimulation pulses comprises:
    determining a value of the second primary current amplitude that is different from a value of the first primary current amplitude;
    determining a value of the second master current amplitude that is different from a value of the first master current amplitude,
    wherein a ratio of the second primary current amplitude to the second master current amplitude is the same as a ratio of the first primary current amplitude to the first master current amplitude.

6. The method of claim 5,
wherein the value of the second primary current amplitude is greater than the value of the first primary current amplitude,
wherein the value of the second master current amplitude is greater than the value of the first master current amplitude, and
wherein the ratio of the second primary current amplitude to the second master current amplitude is the same as the ratio of the first primary current amplitude to the first master current amplitude.

7. The method of claim 5,
wherein the value of the second primary current amplitude is less than the value of the first primary current amplitude,
wherein the value of the second master current amplitude is less than the value of the first master current amplitude, and
wherein the ratio of the second primary current amplitude to the second master current amplitude is the same as the ratio of the first primary current amplitude to the first master current amplitude.

8. The method of claim 1, wherein the method further comprises:
    during the predetermined period of time, delivering, by the medical device, electrical stimulation therapy comprising a third train of electrical stimulation pulses to the patient,
    wherein the third train of electrical stimulation pulses comprises a third pulse frequency less than 500 Hertz; and
    responsive to the predetermined period of time elapsing, ceasing the delivery of the electrical stimulation therapy comprising the third train of electrical stimulation pulses.

9. The method of claim 1, further comprising:
delivering electrical stimulation therapy comprising a plurality of primary electrical stimulation pulses to the patient;
detecting, by the medical device, a change in posture of the patient, wherein:
    delivering the electrical stimulation therapy comprising the first train of electrical stimulation pulses to the patient comprises delivering, in response to the detected change in posture of the patient, the first train of electrical stimulation pulses comprising the plurality of primary electrical stimulation pulses followed by a master electrical stimulation pulse to the patient,
    the plurality of primary electrical stimulation pulses are configured to provide therapy to the patient, and
    the master electrical stimulation pulse is configured to evoke the ECAP signal from the tissue of the patient.

10. The method of claim 1, wherein the electrical stimulation therapy comprises a burst frequency greater than or equal 1 Hertz and less than or equal to 200 Hertz, wherein the burst frequency comprises a frequency at which the first train of electrical stimulation pulses and the second train of electrical stimulation pulses are delivered to the patient.

11. The method of claim 1, wherein the medical device is an implantable medical device.

12. A medical device configured to:
deliver electrical stimulation therapy comprising a first train of electrical stimulation pulses and a second train of electrical stimulation pulses to a patient, wherein the first train of electrical stimulation pulses comprises a first pulse frequency greater than or equal to 500 Hertz, and wherein the first train of electrical stimulation pulses is separated from the second train of electrical stimulation pulse by a predetermined period of time;
after delivering the first train of electrical stimulation pulses, cease the delivery of the electrical stimulation therapy for the predetermined period of time;
during the predetermined period of time, sense an evoked compound action potential (ECAP) signal from a tissue of the patient;
determine, based on a characteristic value of the ECAP signal, a value of at least one parameter at least partially defining the second train of electrical stimulation pulses, wherein the second train of electrical stimulation pulses comprises a second pulse frequency greater than or equal to 500 Hertz; and
responsive to the predetermined period of time elapsing, deliver the second train of electrical stimulation pulses according to the value of the at least one parameter at least partially defining the second set of pulses.

13. The medical device of claim 12,
wherein the ECAP signal comprises a first ECAP signal, and
wherein the medical device is further configured to:
    after delivering the second train of electrical stimulation pulses, cease the delivery of the electrical stimulation therapy for the predetermined period of time;
    during the predetermined period of time, sense a second ECAP signal from the tissue of the patient;
    determine, based on a characteristic value of the second ECAP signal, a value of at least one parameter at least partially defining a third train of electrical stimulation pulses, wherein the third train of electrical stimulation pulses comprises a pulse frequency greater than or equal to 500 Hertz; and responsive to the predetermined period of time elapsing, deliver the third train of electrical stimulation pulses according to the value of the at least one parameter at least partially defining the second set of pulses.

14. The medical device of claim 12, wherein:
the first train of electrical stimulation pulses comprises a plurality of primary electrical stimulation pulses followed by a master electrical stimulation pulse,
the plurality of primary electrical stimulation pulses are defined by a primary set of parameters and configured to contribute to therapy of the patient, and
the master electrical stimulation pulse is defined by a master set of parameters and configured to evoke the ECAP signal from the tissue of the patient, wherein a value of the master set of parameters is different than a value of the primary set of parameters.

15. The medical device of claim 14, wherein the master electrical stimulation pulse of the first train comprises a current amplitude greater than a pulse amplitude of the plurality of primary electrical stimulation pulses of the first train.

16. The medical device of claim 14,
wherein the plurality of primary electrical stimulation pulses of the first train is a first primary current amplitude,
wherein the master electrical stimulation pulse of the first train comprises a first master current amplitude,
wherein the plurality of primary electrical stimulation pulses of the second train comprises a second primary current amplitude,
wherein the master electrical stimulation pulse of the second train comprises a second master current amplitude, and
wherein to determine the value of the at least one parameter defining the second train of electrical stimulation pulses, the medical device is configured to:
determine a value of the second primary current amplitude that is different from a value of the first primary current amplitude; and
determine a value of the second master current amplitude that is different from a value of the first master current amplitude,
wherein a ratio of the second primary current amplitude to the second master current amplitude is the same as a ratio of the first primary current amplitude to the first master current amplitude.

17. The medical device of claim 16,
wherein the value of the second primary current amplitude is greater than the value of the first primary current amplitude,
wherein the value of the second master current amplitude is greater than the value of the first master current amplitude, and
wherein the ratio of the second primary current amplitude to the second master current amplitude is the same as the ratio of the first primary current amplitude to the first master current amplitude.

18. The medical device of claim 16,
wherein the value of the second primary current amplitude is less than the value of the first primary current amplitude,
wherein the value of the second master current amplitude is less than the value of the first master current amplitude, and
wherein the ratio of the second primary current amplitude to the second master current amplitude is the same as the ratio of the first primary current amplitude to the first master current amplitude.

19. The medical device of claim 12, wherein the medical device is further configured to:
during the predetermined period of time, deliver electrical stimulation therapy comprising a third train of electrical stimulation pulses to the patient, wherein the third train of electrical stimulation pulses comprises a third pulse frequency less than 500 Hertz; and
responsive to the predetermined period of time elapsing, cease the delivery of the electrical stimulation therapy comprising the third train of electrical stimulation pulses.

20. A non-transitory, computer-readable medium comprising instructions that, when executed, are configured to cause processing circuitry of an implantable medical device to:
control a stimulation generator of the implantable medical device to deliver electrical stimulation therapy comprising a first train of electrical stimulation pulses and a second train of electrical stimulation pulses to a patient, wherein the first train of electrical stimulation pulses comprises a first pulse frequency greater than or equal to 500 Hertz, and wherein the first train of electrical stimulation pulses is separated from the second train of electrical stimulation pulse by a predetermined period of time;
after delivering the first train of electrical stimulation pulses, control the stimulation generator to cease the delivery of the electrical stimulation therapy for the predetermined period of time;
during the predetermined period of time, sense an evoked compound action potential (ECAP) signal from a tissue of the patient;
determine, based on a characteristic value of the ECAP signal, a value of at least one parameter at least partially defining the second train of electrical stimulation pulses, wherein the second train of electrical stimulation pulses comprises a second pulse frequency greater than or equal to 500 Hertz; and
responsive to the predetermined period of time elapsing, control the stimulation generator to deliver the second train of electrical stimulation pulses according to the value of the at least one parameter at least partially defining the second set of pulses.

* * * * *